United States Patent [19]
Wehner et al.

[11] Patent Number: 6,034,238
[45] Date of Patent: Mar. 7, 2000

[54] HETEROCYCLIC COMPOUNDS, THEIR PREPARATION AND THEIR USE AS LEUCOCYTE ADHESION INHIBITORS AND VLA-4-ANTAGONISTS

[75] Inventors: Volkmar Wehner, Sandberg; Hans Ulrich Stilz; Wolfgang Schmidt, both of Frankfurt; Dirk Seiffge, Mainz-Kostheim, all of Germany

[73] Assignee: Hoechst Marion Roussel Deutschland GmbH, Frankfurt am Main, Germany

[21] Appl. No.: 09/158,772

[22] Filed: Sep. 23, 1998

[30] Foreign Application Priority Data

Sep. 23, 1997 [DE] Germany ............... 197 41 873

[51] Int. Cl.⁷ ............... C07D 413/00; C07D 233/40; C07D 233/84; A61K 31/535; A61K 31/415
[52] U.S. Cl. ............... 544/139; 514/235.8; 514/397; 514/399; 514/400; 548/312.7; 548/319.1; 548/320.1; 548/321.1
[58] Field of Search ............... 548/319.1, 321.1, 548/320.1, 312.7; 514/397, 399, 400, 235.8; 544/139

[56] References Cited

U.S. PATENT DOCUMENTS

| | | | |
|---|---|---|---|
| 4,344,949 | 8/1982 | Hoefle et al. | 424/258 |
| 4,350,704 | 9/1982 | Hoefle et al. | 424/274 |
| 4,374,847 | 2/1983 | Gruenfeld | 424/274 |
| 5,389,614 | 2/1995 | Koenig et al. | 514/18 |
| 5,397,796 | 3/1995 | Zoller et al. | 514/389 |
| 5,424,293 | 6/1995 | Zoller et al. | 514/20 |
| 5,554,594 | 9/1996 | Zoller et al. | 514/18 |
| 5,658,935 | 8/1997 | Klinger et al. | 514/359 |
| 5,686,421 | 11/1997 | Koenig et al. | 514/18 |
| 5,731,311 | 3/1998 | Mohan et al. | 514/235.8 |

FOREIGN PATENT DOCUMENTS

| | | |
|---|---|---|
| 0 029 488 | 6/1981 | European Pat. Off. . |
| 0 031 741 | 7/1981 | European Pat. Off. . |
| 0 046 953 | 3/1982 | European Pat. Off. . |
| 0 049 605 | 4/1982 | European Pat. Off. . |
| 0 049 658 | 4/1982 | European Pat. Off. . |
| 0 050 800 | 5/1982 | European Pat. Off. . |
| 0 052 870 | 6/1982 | European Pat. Off. . |
| 0 079 022 | 5/1983 | European Pat. Off. . |
| 0 084 164 | 7/1983 | European Pat. Off. . |
| 0 089 637 | 9/1983 | European Pat. Off. . |
| 0 090 341 | 10/1983 | European Pat. Off. . |
| 0 090 362 | 10/1983 | European Pat. Off. . |
| 0 105 102 | 4/1984 | European Pat. Off. . |
| 0 109 020 | 5/1984 | European Pat. Off. . |
| 0 111 873 | 6/1984 | European Pat. Off. . |
| 0 271 865 | 6/1988 | European Pat. Off. . |
| 0 344 682 | 12/1989 | European Pat. Off. . |
| 0 449 079 | 10/1991 | European Pat. Off. . |
| 0 796 855 | 9/1997 | European Pat. Off. . |
| 0 842 943 | 11/1997 | European Pat. Off. . |
| 0 842 944 | 11/1997 | European Pat. Off. . |
| 0 842 945 | 11/1997 | European Pat. Off. . |
| 235 866 | 5/1986 | Germany . |
| 93/13798 | 7/1993 | WIPO . |
| WO 93/15764 | 8/1993 | WIPO . |
| 93/18057 | 9/1993 | WIPO . |
| 94/15958 | 7/1994 | WIPO . |
| WO 94/16094 | 7/1994 | WIPO . |
| WO 94/17828 | 8/1994 | WIPO . |
| 95/14008 | 5/1995 | WIPO . |
| 95/15973 | 6/1995 | WIPO . |
| WO 95/19790 | 7/1995 | WIPO . |
| 96/00581 | 1/1996 | WIPO . |
| 96/06108 | 2/1996 | WIPO . |
| 96/20216 | 7/1996 | WIPO . |
| 96/22966 | 8/1996 | WIPO . |
| 96/33976 | 10/1996 | WIPO . |
| 97/03094 | 1/1997 | WIPO . |
| 98/04247 | 2/1998 | WIPO . |
| 98/04913 | 2/1998 | WIPO . |
| 98/42656 | 10/1998 | WIPO . |

OTHER PUBLICATIONS

Albelda, S., et al., "Molecular and Cellular Properties of Pecam–1 (endoCAM/CD31): A Novel Vascular Cell–Cell Adhesion Molecule," Journal of Cell Biology, vol. 114, No. 5, pp. 1059–1068 (1991).

Anna, C., et al., "The VLA–4/VCAM–1 Pathway is Involved in Lymphocyte Adhesion to Endothelium in Rheumatoid Synovium," Journal of Immunology, vol. 147, No. 12, pp. 4207–4210 (1991).

(List continued on next page.)

Primary Examiner—Floyd D. Higel
Attorney, Agent, or Firm—Foley & Lardner

[57] ABSTRACT

Compounds of the formula I,

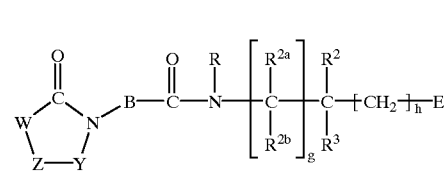

(I)

in which B, E, W, Y, Z, R, $R^2$, $R^{2a}$, $R^{2b}$, $R^3$, g and h have the meanings indicated in the specifications. The compounds of the formula I are valuable pharmaceutical active compounds, which are suitable, for example, for the therapy and prophylaxis of inflammatory disorders, for example of rheumatoid arthritis, or of allergic disorders. The compounds of the formula I are inhibitors of the adhesion and migration of leucocytes and/or antagonists of the adhesion receptor VLA-4 belonging to the integrins group. They are generally suitable for the therapy or prophylaxis of illnesses which are caused by an undesired extent of leucocyte adhesion and/or leucocyte migration or are associated therewith, or in which cell-cell or cell-matrix interactions which are based on interactions of VLA-4 receptors with their ligands play a part. The invention furthermore relates to processes for the preparation of the compounds of the formula I, their use in the therapy and prophylaxis of the disease states mentioned and pharmaceutical preparations which contain the compounds of the formula I.

15 Claims, No Drawings

OTHER PUBLICATIONS

Barbadillo, C., et al., "Anti–Integrin Immunotherapy in Rheumatoid Arthritis: Protective Effect of Anti–α–4 Antibody in Adjuvant Arthritis," Springer Seminars in Immunotherapy, vol. 16 pp. 427–436 (1985).

Bergelson, J., et al., "Do Integrins Use a 'Midas Touch' to Grasp an Asp?" Current Biology, vol. 5, No. 6, pp. 615–617 (1995).

Bergeron, R., et al., "Total Synthesis of (±)–15–Deoxyspergualin," J. Org. Chem., vol. 52, pp. 1700–1703 (1987).

Borne, R., et al., "Conformational Analogues of Antihypertensive Agents Related to Guanethidine<" Journal of Medicinal Chemistry, vol. 20, No. 6, pp. 771–776 (1977).

Bundgaard, H., "Novel Chemical Approaches in Prodrug Design," Drugs of the Future, vol. 16, No. 5, pp. 443–458 (1991).

Büllesbach, E. "Protection in Peptide Synthesis (Part II): Multifunctional Amino Acids—Cleavage of Protecting Groups—Outlook on the Technique of Protection," Kontakte, vol. 1, No. 80, pp. 23–35 (1980).

Damle, N., et al., "Vascular Cell Adhesion Molecule 1 Induces T–cell Antigen Receptor–Dependent Activation of CD4+T Lymphocytes," Proc. Nat'l. Acad. Sci. USA, vol. 88, pp. 6403–6407 (1991).

Davies, S., et al., "Asymmetric Synthesis of R–β–Amino Butanoic Acid and S–β–Tyrosine: Homochiral Lithium Amide Equivalents for Michael Additions to a,β–Unsaturated Esters," Tetrahedron: Asymmetry, vol. 2, No. 3, pp. 183–186 (1991).

Elices, M.J., et al., "The Integrin VLA–4 Mediates Leukocyte Recruitment to Skin Inflammatory Sites In Vivo," Clinical and Experimental Rheumatology, vol. 11, Supp. 8, pp. S77–S80 (1993).

Elices, M.J., et al., "Expression and Functional Significance of Alternatively Spliced CS1 Fibronectin in Rheumatoid Arthritis Microvasculature," J. Clin. Invest., vol. 93, pp. 405–416 (1994).

Elices, M.J., "The Integrin $\alpha_4\beta_1$ (VLA–4) As a Therapeutic Target," Ciba Foundation Symposium, vol. 189, pp. 79–90 (1995).

Fleisher, D., et al., "Improved Oral Drug Delivery: Solubility Limitations Overcome by the Use of Prodrugs," Advanced Drug Delivery Reviews, vol. 19, pp. 115–130 (1996).

Freedman, A., et al., "Follicular Non–Hodgkin's Lymphoma Cell Adhesion to Normal Germinal Centers and Neoplastic Follicles Involves Very Late Antigen–4 and Vascular Cell Adhesion Molecule–1," Blood, vol. 79, No. 1, pp. 206–212 (1992).

Goldschmidt, V.S., et al., "Über Peptid–Synthesen I," Liebigs. Ann. Chem., vol. 575, pp. 217–231 (1952).

Hafner, L.S., et al., "Preparation of 2–Imino– and 2–Nitrimino–1,3–diazacycloalkanes," J. Am. Chem. Soc., vol. 79, pp. 1157–1159 (1957).

Harlan, J., "Leukocyte–Endothelial Interactions," Blood, vol. 65, No. 3, pp. 513–525 (1985).

Hubbuch, A., "Schutzgruppen in der Peptidsynthese (Part I): Schutzgruppentaktik, Amino– and Carboxyl–Schutzgruppan," Kontakte, vol. 3, No. 79, pp. 14–23 (1979).

Isobe, M., et al, "Effect of Anti–VCAM–1 and Anti–VLA–4 Monoclonal Antibodies on Cardiac Allograft Survival and Response to Soluble Antigens in Mice," Transplantation Proceedings, vol. 26, No. 2, pp. 867–868 (1994).

Issekutz, T., "Inhibition of In Vivo Lymphocyte Migration to Inflammation and Homing to Lymphoid Tissues by the TA–2 Monoclonal Antibody," Journal of Immunology, vol. 147, No. 12, pp. 4178–4184 (1991).

Kim, K., et al., "Monosubstituted Guanidines from Primary Amines and Aminoiminomethanesulfonic Acid," Tetrahedron Letters, vol. 29, No. 26, pp. 3183–3186 (1988).

Kuijpers, T., "Pathophysiological Aspects of VLA–4 Interactions and Possibilities for Therapeutical Interventions," Springer Seminars in Immunopathology, vol. 16, pp. 379–389 (1995).

Laffon, A., et al., "Upregulated Expression and Function of VLA–4 Fibronectin Receptors on Human Activated T–Cells in Rheumatoid Arthritis," J. Clin. Invest., vol. 88, pp. 546–552 (1991).

Morales–Ducret, J., et al., "$\alpha_4/\beta_1$ Integrin (VLA–4) Ligands in Arthritis: Vascular Cell Adhesion Molecule–1 Expression in Synovium and on Fibroblast–Like Synoviocytes," Journal of Immunology, vol. 149, No. 4, pp. 1424–1431 (1992).

Muacevic, G., "New Apparatus and Method for the Toxicological Investigation of Metered Aerosols in Rats," Arch. Toxicol., vol. 34, pp. 1–8, (1975).

Nielson, N., et al., "Glycolamide Esters as Biolabile Prodrugs of Carboxylic Acid Agents: Synthesis, Stability, Bioconversion, and Physiochemical Properties," Journal of Pharmaceutical Sciences, vol. 77, No. 4, pp. 285–298 (1988).

Nowick, J., et al., "Synthesis of Peptide Isocyanates and Isothiocynates," J. Org. Chem, vol. 61, pp. 3929–3934 (1996).

O'Brien, K., et al., "Vascular Cell Adhesion Molecule–1 is Expressed in Human Coronary Atherosclerotic Plaques," J. Clin. Invest., vol. 92, pp. 945–951 (1993).

Ockenhouse, C., et al., "Human Vascular Endothelial Cell Adhesion Receptors for *Plasmodium falciparum*–infected Erythrocytes: Roles for Endothelial Leukocyte Adhesion Molecule 1 and Vascular Cell Adhesion Molecule 1," Journal of Experimental Medicine, vol. 176, pp. 1183–1189 (1992).

Osborn, L., et al., "Direct Expression Cloning of Vascular Cell Adhesion Molecule 1, a Cytokine–Induced Endothelial Protein that Binds to Lymphocytes," Cell, vol. 59, pp. 1203–1211 (1989).

Osborn, L., "Leukocyte Adhesion to Endothelium in Inflammation," Cell, vol. 62, pp. 3–6 (1990).

Postigo, A., et al., Increased Binding of Synovial T. Lymphocytes from Rheumatoid Arthritis to Endothelial–Leukocyte Adhesion Molecule–1 (ELAM–1) and Vascular Cell Adhesion Molecule–1 (VCAM–1), J. Clin. Invest., vol. 89, pp. 1445–1452 (1992).

Renkonen, R., et al., "Rapid Communication: Expression of Endothelial Adhesion Molecules In Vivo," Journal of Pathology, vol. 140, No. 4, pp. 763–767 (1992).

Rice, G., et al., "An Inducible Endothelial Cell Surface Glycoprotein Mediates Melanoma Adhesion," Science, vol. 246, pp. 1303–1306 (1989).

Ruoslahti, E., "Fibronectin and its Receptors," Ann. Rev. Biochem., vol. 57, pp. 375–413 (1988).

Safadi, M., et al., "Phosphoryloxymethyl Carbamates and Carbonates—Novel Water–Soluble Prodrugs for Amimes and Hindered Alcohols," Pharmaceutical Research, vol. 10, No. 9, pp. 1350–1354 (1993).

Saulnier, M., et al., "An Efficient Method for the Synthesis of Guanidino Prodrugs," Bioorganic & Medicinal Chemistry Letters, vol. 4, No. 16, pp. 1985–1990 (1994).

Scott, F., et al., "Studies in the Pyrazole Series," Pyrazole Series: Substituted Guanidines, vol. 75, pp. 4053–4054 (1953).

Seiffge, D., et al., "Effects of Different Mediators or Cytokines and Monoclonal Antibodies to Adhesion Molecules on Leukocyte Adhesion in Rat Mesenteric Venules," Int. J. Microcirc., vol. 15, pp. 301–308 (1995).

Springer, T., "Traffic Signals for Lymphocyte Recirculation and Leukocyte Emigration: The Multistep Paradigm," Cell, vol. 76, pp. 301–314 (1994).

Stoolman, L., "Adhesion Molecules Controlling Lymphocyte Migration," Cell, vol. 56, pp. 907–910 (1989).

Takeuchi, T., et al., "Upregulated Expression and Function of Integrin Adhesive Receptors in Systemic Lupus Erythematosus Patients with Vasculitis," J. Clin. Invest., vol. 92, pp. 3008–3016 (1993).

Tropp, C., "Einwirkung von Phosgen auf Polypeptidartige Derivate der p–Amino–benzosäure: Bildung von 1.3–substi–tuierten Hydantoinen," Chem. Ber, vol. 61, pp. 1431–1439 (1928).

Von Hans, T., et al., "Über die Bildung Substituierter Hydantoine aus Aldehyden und Ketonen," Journal für prakishche Chemie N.F., vol. 141, pp. 5–43 (1934).

Wagner, G., et al., "Syntheses von 3–[Amidinophenyl]–alaninen und 3–[Amidinophenyl]–milchsären," Pharmaze, vol. 29, No. 1, pp. 12–15 (1974).

Weiss, S., et al., "Zur Guanylierung von Aminen mit O–Methyl–isoharnstoff–sulfat," Chemiker–Zeitung, vol. 98, No. 12, pp. 617–618 (1974).

Wollweber, H., et al., "2–(Guanidino)–anilide und Verwandte Verbindungen," Arzneim–Forsch./Drug Res., vol. 34, No. 5, (1984).

Yang, X., et al., "Inhibition of Insulitis and Prevention of Diabetes in Nonobese Diabetic Mice by Blocking L–selectin and Very Late Antigen–4 Adhesion Receptors," Proc. Nat'l. Acad. Sci. USA, vol. 90, pp. 10494–10498 (1993).

Yednock, T., et al., "Prevention of Experimental Autoimmune Encephalomyelitis by Antibodies Against $\alpha_4\beta_1$ Integrin," Nature, vol. 356, pp. 63–66 (1992).

Zettlmeissl, G., et al., "Expression and Characterization of Human CD4: Immunoglobulin Fusion Proteins," DNA and Cell Biology, vol. 9, No. 5, pp. 347–353 (1990).

Cronstein, Bruce N. et al., "The Adhesion Molecules of Inflammation". Arthritis and Rheumatism, vol. 36(2); pp. 147–157(1993).

Elices, Mariano J. et al., "VCAM–1 on Activated Endothelium Interacts with the Leukocyte Integrin VLA–4 at a Site Distinct from the VLA–4/Fibronectin Binding Site". Cell, vol. 60; pp. 577–584(1990).

Foster, Carolyn A. et al., "VCAM–1/α4–integrin adhesion pathway: Therapeutic target for allergic inflammatory disorders". Jour. Allergy Clin. Immunol., vol. 96(6); pp. S270–S277(1996).

Kilger et al., "Molecular analysis of the physiological and pathophysiological role of α4–integrins". J. Mol. Med., vol. 73; pp. 347–354(1995).

Issekutz, Thomas B. et al., Rat Blood Neutrophils Express Very Late Antigen 4 and it Mediates Migration to Arthritic Joint and Dermal Inflammation. J. Exp. Med., vol. 183; pp. 2175–2184(1996).

McMurray, Robert W., "Adhesion Molecules in Autoimmune Disease". Seminars in Arthritis and Rheumatism, vol. 25(4); pp. 215–233 (1996).

HETEROCYCLIC COMPOUNDS, THEIR PREPARATION AND THEIR USE AS LEUCOCYTE ADHESION INHIBITORS AND VLA-4-ANTAGONISTS

BACKGROUND OF THE INVENTION

1. Field of the Invention

The present invention relates to compounds of the formula I,

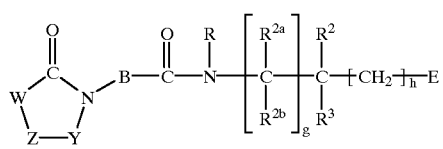

in which B, E, W, Y, Z, R, $R^2$, $R^{2a}$, $R^{2b}$, $R^3$, g and h have the meanings indicated below. The compounds of the formula I are valuable pharmaceutical active compounds, which are suitable, for example, for the therapy and prophylaxis of inflammatory disorders, for example of rheumatoid arthritis, or of allergic disorders. Compounds of the formula I are inhibitors of the adhesion and migration of leukocytes and/or antagonists of the adhesion receptor VLA4 belonging to the integrin group of receptors. They are generally suitable for the therapy or prophylaxis of illnesses which are caused by an undesired extent of leukocyte adhesion and/or leukocyte migration or are associated therewith, or in which cell-cell or cell-matrix interactions which are based on interactions of VLA4 receptors with their ligands play a part. The invention furthermore relates to processes for the preparation of the compounds of the formula I, their use in the therapy and prophylaxis of the disease states mentioned, and to pharmaceutical preparations which contain the compounds of the formula I.

2. Description of Related Art

The integrins are a group of adhesion receptors which play an important part in cell-cell-binding and cell-extracellular matrix-binding processes. They have an αβ-heterodimeric structure and exhibit a wide cellular distribution and are closely structurally related. The integrins include, for example, the fibrinogen receptor on platelets, which interacts especially with the RGD sequence of fibrinogen, or the vitronectin receptor on osteoclasts, which interacts especially with the RGD sequence of vitronectin or of osteopontin. The integrins are divided into three major groups; the β2 subfamily with the representatives LFA-1, Mac-1 and p150/95, which are responsible in particular for cell-cell interactions of the immune system; and the subfamilies β1 and β3, whose representatives mainly mediate cell adhesion to components of the extracellular matrix (Ruoslahti, Annu. Rev. Biochem. 1988, 57, 375). The integrins of the β1 subfamily, also called VLA proteins (very late (activation) antigen), include at least six receptors which interact specifically with fibronectin, collagen and/or laminin as ligands. Within the VLA family, the integrin VLA4 (α4β1) is atypical, insofar as it is mainly restricted to lymphoid and myeloid cells and is responsible in these cells for cell-cell interactions with a large number of other cells. For example, VLA4 mediates the interaction of T and B lymphocytes with the heparin II-binding fragment of human plasma fibronectin (FN). The binding of VLA4 with the heparin II-binding fragment of plasma fibronectin is especially based on an interaction with an LDVP sequence. In contrast to the fibrinogen or vitronectin receptor, VLA-4 is not a typical RGD-binding integrin (Kilger and Holzmann, J. Mol. Meth. 1995, 73, 347).

The leucocytes circulating in the blood normally exhibit only a low affinity for the vascular endothelial cells which line the blood vessels. Cytokines which are released from inflamed tissue cause the activation of endothelial cells and thus the expression of a large number of cell surface antigens. These include, for example, the adhesion molecules ELAM-1 (endothelial cell adhesion molecule-1; also designated as E-selectin), which, inter alia, binds neutrophiles, ICAM-1 (intercellular adhesion molecule-1), which interacts with LFA-1 (leucocyte function-associated antigen 1) on leucocytes, and VCAM-1 (vascular cell adhesion molecule-1), which binds various leucocytes, inter alia lymphocytes (Osborn et al., Cell 1989, 59, 1203). VCAM-1, like ICAM-1, is a member of the immunoglobulin gene superfamily. VCAM-1 (first known as INCAM-110) was identified as an adhesion molecule which is induced on endothelial cells by inflammatory cytokines such as TNF and IL-1 and lipopolysaccharides (LPS). Elices et al. (Cell 1990, 60, 577) showed that VLA4 and VCAM-1 form a receptor-ligand pair which mediates the adhesion of lymphocytes to activated endothelium. The binding of VCAM-1 to VLA-4 does not occur via an interaction of the VLA-4 with an RGD sequence; VCAM-1 does not contain such a sequence (Bergelson et al., Current Biology 1995, 5, 615). VLA4, however, also occurs on other leucocytes, and the adhesion of leucocytes other than lymphocytes is also mediated via the VCAM-1/VLA4 adhesion mechanism. VLA4 thus represents an individual example of a β1 integrin receptor which, via the ligands VCAM-1 and fibronectin, plays an important part both in cell-cell interactions and in cell-extracellular matrix interactions.

The cytokine-induced adhesion molecules play an important part in the recruitment of leucocytes into extravascular tissue regions. Leucocytes are recruited into inflammatory tissue regions by cell adhesion molecules which are expressed on the surface of endothelial cells and serve as ligands for leucocyte cell surface proteins or protein complexes (receptors) (the terms ligand and receptor are interchangeable in this context). Leucocytes from the blood first must adhere to endothelial cells before they can migrate into the synovium. Since VCAM-1 binds to cells which carry the integrin VLA-4 (α4β1), such as eosinophils, T and B lymphocytes, monocytes or else neutrophils, it and the VCAM-1/VLA-4 mechanism have the function of recruiting cells of this type from the blood stream into areas of infection and inflammatory foci (Elices et al., Cell 1990, 60, 577; Osborn, Cell 1990, 62, 3; Issekutz et al., J. Exp. Med. 1996, 183, 2175).

The VCAM-1/VLA4 adhesion mechanism has been connected with a number of physiological and pathological processes. Apart from cytokine-induced endothelium, VCAM-1 is additionally expressed, inter alia, from the following cells: myoblasts, lymphoid dendritic cells and tissue macrophages, rheumatoid synovium, cytokine-stimulated neural cells, parietal epithelial cells of the Bowman's capsule, the renal tubular epithelium, inflamed tissue during heart and kidney transplant rejection and by intestinal tissue in graft-versus-host disease. VCAM-1 is also found to be expressed on those tissue areas of the arterial endothelium which correspond to early arteriosclerotic plaques of a rabbit model. Additionally, VCAM-1 is expressed on follicular dendritic cells of human lymph nodes and is found on stroma cells of the bone marrow, for example in the mouse. The latter finding points to a function of VCAM-1 in B-cell development. Apart from cells of hematopoietic origin, VLA4 is also found, for example, on melanoma cell lines, and the VCAM-1VLA-4 adhesion mechanism is connected with the metastasis of such tumors (Rice et al., Science 1989, 246, 1303).

The main form in which VCAM-1 occurs in vivo on endothelial cells, and which is the dominant form in vivo, is designated as VCAM-7D and contains seven immunoglobulin domains. The domains 4, 5 and 6 are similar in their amino acid sequences to the domains 1, 2 and 3. The fourth domain is removed in a further form, consisting of six domains, designated here as VCAM-6D, by alternative splicing. VCAM-6D can also bind VLA4-expressing cells.

Further details on VLA-4, VCAM-1, integrins and adhesion proteins are found, for example, in the articles by Kilger and Holzmann, J. Mol. Meth. 1995, 73, 347; Elices, Cell Adhesion in Human Disease, Wiley, Chichester 1995, p. 79; Kuijpers, Springer Semin. Immunopathol. 1995, 16, 379.

On account of the role of the VCAM-1/VLA4 mechanism in cell adhesion processes, which are of importance, for example, in infections, inflammations or atherosclerosis, it has been attempted by means of interventions into these adhesion processes to control illnesses, in particular, for example, inflammations (Osborn et al., Cell 1989, 59,1203). A method of doing this is the use of monoclonal antibodies which are directed against VLA4. Monoclonal antibodies (mAB), of this type, which as VLA-4 antagonists block the interaction between VCAM-1 and VLA4, are known. Thus, for example, the anti-VLA4 mAB HP2/1 and HP1/3 inhibit the adhesion of VLA-4-expressing Ramos cells (B-cell-like cells) to human umbilical cord endothelial cells and to VCAM-1-transfected COS cells. The anti-VCAM-1 mAB 4B9 likewise inhibits the adhesion of Ramos cells, Jurkat cells (T-cell-like cells) and HL60 cells (granulocyte-like cells) to COS cells transfected with genetic constructs which cause VCAM-6D and VCAM-7D to be expressed. In vitro data with antibodies which are directed against the $\alpha 4$ subunit of VLA-4 show that the adhesion of lymphocytes to synovial endothelial cells is blocked, an adhesion which plays a part in rheumatoid arthritis (van Dinther-Janssen et al., J. Immunol. 1991,147, 4207).

In vivo experiments have shown that an experimental autoimmune encephalomyelitis can be inhibited by anti-$\alpha 4$ mAB. The migration of leucocytes into an inflammatory focus is likewise blocked by a monoclonal antibody against the $\alpha 4$ chain of VLA4. The influencing of the VLA4-dependent adhesion mechanism by antibodies was also investigated in an asthma model in order to investigate the role of VLA4 in the recruitment of leucocytes into inflamed lung tissue (U.S. Pat. Ser. No. 07/821,768; EP-A-626 861). The administration of anti-VLA-4 antibodies inhibited the late-phase reaction and airway overreaction in allergic sheep.

The VLA-4-dependent cell adhesion mechanism was also investigated in a primate model of inflammatory bowel disease (IBD). In this model, which corresponds to ulcerative colitis in man, the administration of anti-VLA4 antibodies resulted in a significant reduction in the acute inflammation.

Moreover, it was possible to show that VLA4-dependent cell adhesion plays a part in the following clinical conditions including the following chronic inflammatory processes: rheumatoid arthritis (Cronstein and Weismann, Arthritis Rheum. 1993, 36,147; Elices et al., J. Clin. Invest. 1994, 93, 405), diabetes mellitus (Yang et al., Proc. Natl. Acad. Sci. USA 1993, 90, 10494), systemic lupus erythematosus (Takeuchi et al., J. Clin. Invest. 1993, 92, 3008), allergies of the delayed type (type IV allergy) (Elices et al., Clin. Exp. Rheumatol. 1993, 11, S77), multiple sclerosis (Yednock et al., Nature 1992, 356, 63), malaria (Ockenhouse et al., J. Exp. Med. 1992,176,1183), arteriosclerosis (O'Brien et al., J. Clin. Invest. 1993, 92, 945), transplantation (Isobe et al., Transplantation Proceedings 1994, 26, 867–868), various malignancies, for example melanoma (Renkonen et al., Am. J. Pathol. 1992, 140, 763), lymphoma (Freedman et al., Blood 1992, 79, 206) and others (Albelda et al., J. Cell Biol. 1991,114, 1059).

VLA-4 blocking by suitable antagonists accordingly offers effective therapeutic possibilities, in particular, for example, of treating various inflammatory conditions including asthma and IBD. The particular relevance of VLA-4 antagonists for the treatment of rheumatoid arthritis in this case results, as already stated, from the fact that leucocytes from the blood must first adhere to endothelial cells before they can migrate into the synovium, and that the VLA4 receptor plays a part in this adhesion. The fact that VCAM-1 is induced by inflammatory agents on endothelial cells (Osborn, Cell 1990, 62, 3; Stoolman, Cell 1989, 56, 907), and the recruitment of various leucocytes into areas of infection and inflammatory foci has already been discussed above. In this respect, T cells adhere to activated endothelium mainly via the LFA-1/ICAM-1 and VLA-4/VCAM-1 adhesion mechanisms (Springer, Cell 1994, 76, 301). On most synovial T cells, the binding capacity of VLA-4 for VCAM-1 is increased in rheumatoid arthritis (Postigo et al., J. Clin. Invest. 1992, 89, 1445). Additionally, an increased adhesion of synovial T cells to fibronectin has been observed (Laffon et al., J. Clin. Invest. 1991, 88, 546; Morales-Ducret et al., J. Immunol. 1992, 149,1424). VLA-4 is upregulated both in the course of its expression and with respect to its function on T lymphocytes of the rheumatoid synovial membrane. The blocking of the binding of VLA-4 to its physiological ligands VCAM-1 and fibronectin makes possible an effective prevention or alleviation of articular inflammatory processes. This is also confirmed by experiments with the antibody HP2/1 on Lewis rats with adjuvant arthritis, in which an effective prevention of illness has been observed (Barbadillo et al., Springer Semin. Immunopathol. 1995, 16, 427). VLA-4 is thus an important therapeutic target molecule.

The abovementioned VLA-4 antibodies and the use of antibodies as VLA4 antagonists are described in the Patent Applications WO-A-93/13798, WO-A-93/15764, WO-A-94/16094, WO-A-94/17828 and WO-A-95/19790. In the Patent Applications WO-A-94/15958, WO-A-95/15973, WO-A-96/00581, WO-A-96/06108 and WO-A-96/20216, peptide compounds are described as VLA4 antagonists. The use of antibodies and peptide compounds as pharmaceuticals, however, is afflicted with disadvantages, for example lack of oral availability, rapid degradation or immunogenicity on longer-term use. There is thus a need for VLA4 antagonists having a favorable profile of properties for use in therapy and prophylaxis.

WO-A-94/21607 and WO-A-95/14008 describe substituted 5-membered ring heterocycles, EP-A-449 079, EP-A-530 505 (U.S. Pat. No. 5,389,614), WO-A-93/18057, EP-A-566 919 (U.S. Pat. No. 5,397,796), EP-A-580 008 (U.S. Pat. No. 5,424,293) and EP-A-584 694 (U.S. Pat. No. 5,554,594) describe hydantoin derivatives which have platelet aggregation-inhibitory actions. EP-A-842 943 (German Patent Application 19647380.2) describes that compounds of this type surprisingly also inhibit leucocyte adhesion and are VLA4 antagonists. Further investigations showed that the compounds of the present invention are also strong inhibitors of leucocyte adhesion and VLA4 antagonists.

SUMMARY OF THE INVENTION

The present invention relates to compounds of the formula I,

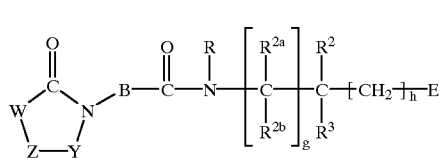

(I)

in which

W is $R^1$—A—$C(R^{13})$ or $R^1$—A—CH=C

Y is a carbonyl group, thiocarbonyl group or methylene group;

Z is $N(R^0)$, oxygen, sulfur or a methylene group;

A is a divalent radical from the group consisting of $(C_1-C_6)$-alkylene, $(C_3-C_7)$-cycloalkylene, phenylene, phenylene-$(C_1-C_6)$-alkyl, $(C_1-C_6)$-alkylene-phenyl, phenylene-$(C_2-C_6)$-alkenyl or a divalent radical of a 5-membered or 6-membered saturated or unsaturated heterocycle which can contain one or two nitrogen atoms and can be monosubstituted or disubstituted by $(C_1-C_6)$-alkyl or doubly bonded oxygen or sulfur;

B is a divalent $(C_1-C_6)$-alkylene radical which can be unsubstituted or substituted by $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl or heteroaryl-$(C_1-C_6)$-alkyl optionally substituted in the heteroaryl radical;

E and $E^a$ independently of one another are tetrazolyl, $(R^dO)_2P(O)$, $HOS(O)_2$, $R^9NHS(O)_2$ or $R^{10}CO$;

$R^0$ is hydrogen, $(C_1-C_8)$-alkyl, $(C_3-C_{12})$-cycloalkyl, $(C_{3-12})$-cycloalkyl-$(C_1-C_8)$-alkyl, $(C_1-C_8)$-bicycloalkyl, $(C_1-C_8)$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, H—CO, $(C_1-C_8)$-alkyl-CO, $(C_3-C_{12})$-cycloalkyl-CO, $(C_{3-12})$-cycloalkyl-$(C_1-C_8)$-alkyl-CO, $(C_6-C_{12})$-bicycloalkyl-CO, $(C_6-C_{12})$-bicycloalkyl-$(C_1-C_8)$-alkyl-CO, $(C_1-C_8)$-tricycloalkyl-CO, $(C_6-C_{12})$-tricycloalkyl-$(C_1-C_8)$-alkyl-CO, optionally substituted $(C_6-C_{14})$-aryl-CO, $(C_6-C_{14})$-aryl-$(C_1-C_8)$-alkyl-CO optionally substituted in the aryl radical, optionally substituted heteroaryl-CO, heteroaryl-$(C_1-C_8)$-alkyl-CO optionally substituted in the heteroaryl radical, $(C_1-C_8)$-alkyl-$S(O)_n$, $(C_3-C_{12})$-cycloalkyl-$S(O)_n$, $(C_3-C_{12})$-cycloalkyl-$(C_1-C_8)$-alkyl-$S(O)_n$, $(C_6-C_{12})$-bicycloalkyl-$S(O)_n$, $(C_6-C_{12})$-bicycloalkyl-$(C_1-C_8)$-alkyl-$S(O)_n$, $(C_6-C_{12})$-tricycloalkyl-$S(O)_n$, $(C_6-C_{12})$-tricycloalkyl-$(C_1-C_8)$-alkyl-$S(O)_n$, optionally substituted $(C_6-C_{14})$-aryl-$S(O)_n$, $(C_6-C_{14})$-aryl-$(C_1-C_8)$-alkyl-$S(O)_n$, optionally substituted in the aryl radical, optionally substituted heteroaryl-$S(O)_n$ or heteroaryl-$(C_1-C_8)$-alkyl-$S(O)_n$ optionally substituted in the heteroaryl radical, where n is 1 or 2;

R, $R^a$, $R^b$, $R^c$ and $R^d$ independently of one another are hydrogen, $(C_1-C_8)$-alkyl, $(C_3-C_8)$-cycloalkyl, $(C_3-C_8)$-cycloalkyl-$(C_1-C_8)$-alkyl, optionally substituted $(C_6-C_{14})$-aryl or $(C_6-C_{14})$-aryl-$(C_1-C_8)$-alkyl optionally substituted in the aryl radical;

$R^1$ is X—NH—C(=NH)—$(CH_2)_p$ or $X^1$—NH—$(CH_2)_p$, where p is 0, 1, 2 or 3;

X is hydrogen, $(C_1-C_6)$-alkyl, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl, optionally substituted $(C_6-C_{14})$-arylcarbonyl, optionally substituted $(C_6-C_{14})$-aryloxycarbonyl, $(C_6-C_{14})$-aryl-$(C_1-C_6)$-alkoxycarbonyl which can also be substituted in the aryl radical, $(R^dO)_2P(O)$, cyano, hydroxyl, $(C_1-C_6)$-alkoxy, $(C_6-C_{14})$-aryl-$(C_1-C_6)$-alkoxy which can also be substituted in the aryl radical, or amino;

$X^1$ has one of the meanings of X or is R'—NH—C(=N—R"), where R' and R" independently of one another have the meanings of X;

$R^2$, $R^{2a}$ and $R^{2b}$ independently of one another are hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl or $(C_3-C_8)$-cycloalkyl-$(C_1-C_8)$-alkyl;

$R^3$ is $R^{11}NH$, $(C_9-C_{12})$-cycloalkyl, $(C_9-C_{12})$-cycloalkyl-$(C_1-C_8)$-alkyl, $(C_6-C_{12})$-bicycloalkyl, $(C_1-C_8)$-bicycloalkyl-$(C_1-C_8)$-alkyl, $(C_6-C_{12})$-tricycloalkyl, $(C_6-C_{12})$-tricycloalkyl-$(C_1-C_8)$-alkyl, CO—$N(R^a)$—$R^4$—$E^a$ or CO—$R^5$—$R^6$—$R^7$;

where, however, $R^3$ cannot be 1-adamantyl if simultaneously W is $R^1$—A—$C(R^{13})$, $R^1$—A is 4-amidinophenyl, $R^{13}$ is methyl, Z is NH, Y is a carbonyl group, B is $CH_2$, R and $R^2$ are hydrogen, E is hydroxycarbonyl, g is 0 and h is 1 and, both with respect to the asymmetric carbon atom in the dioxo-imidazolidine ring and with respect to the carbon atom that carries the radicals $R^2$ and $R^3$, the R form and the S form are present in the molar ratio 1:1;

$R^4$ is a divalent $(C_1-C_4)$-alkylene radical which is substituted by a radical selected from the group consisting of $R^{11}NH$, $(C_9-C_{12})$-cycloalkyl, $(C_9-C_{12})$-cycloalkyl-$(C_1-C_8)$, $(C_6-C_{12})$-bicycloalkyl, $(C_1-C_8)$-bicycloalkyl-$(C_1-C_8)$-alkyl, $(C_6-C_{12})$-tricycloalkyl and $(C_1-C_8)$-tricycloalkyl-$(C_1-C_8)$-alkyl and which can additionally be substituted by one or two identical or different $(C_1-C_4)$-alkyl radicals;

$R^4$ is the divalent radical of a natural or unnatural amino acid, an imino acid or an azaamino acid, where free functional groups can be protected by protective groups that are stable under the conditions of peptide synthesis or can be present as esters or amides, and where in the case of an amino acid or azaamino acid the nitrogen atom of the N-terminal amino group carries a radical $R^b$;

$R^6$ independently of $R^5$ has one of the meanings of $R^5$ or is a direct bond;

$R^7$ is $R^8$—NH or Het;

$R^8$ is $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl or $(C_6-C_{12})$-tricycloalkyl-$(C_1-C_8)$-alkyl;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_{12})$-cycloalkyl, $(C_{3-12})$-cycloalkyl-$(C_1-C_8)$-alkyl, $(C_1-C_8)$-bicycloalkyl, $(C_6-C_{12})$-bicycloalkyl-$(C_1-C_8)$-alkyl, $(C_6-C_{12})$-tricycloalkyl or $(C_6-C_{12})$-tricycloalkyl-$(C_1-C_8)$-alkyl;

$R^{10}$ is hydroxyl, $(C_1-C_8)$-alkoxy, $(C_6-C_{14})$-aryl-$(C_1-C_8)$-alkoxy which can also be substituted in the aryl radical, optionally substituted $(C_6-C_{14})$-aryloxy, $(C_1-C_8)$-alkylcarbonyloxy-$(C_1-C_6)$-alkoxy, $(C_6-C_{14})$-arylcarbonyloxy-$(C_1-C_6)$-alkoxy, amino, mono- or di-$((C_1-C_8)$-alkyl)-amino, $R^8$—NH or Het;

$R^{11}$ is $R^{12}NH$—CO, $R^{12}$—NH—CS, $R^{14a}O$—CO, $R^{14b}CO$, $R^{14c}S(O)$, $R^{14d}S(O)_2$, $R^{14e}NH$—S(O) or $R^{14}NH$—$S(O)_2$;

$R^{12}$ is optionally substituted $(C_6–C_{14})$-aryl, $(C_6–C_{14})$-aryl-$(C_1–C_8)$-alkyl which can also be substituted in the aryl radical, optionally substituted heteroaryl, heteroaryl-$(C_1–C_8)$-alkyl optionally substituted in the heteroaryl radical, $(C_2–C_8)$-alkenyl, $(C_2–C_8)$-alkynyl or the radical $R^{15}$;

$R^{13}$ is hydrogen, $(C_1–C_6)$-alkyl, optionally substituted $(C_6–C_{14})$-aryl, $(C_6–C_{14})$-aryl-$(C_1–C_8)$-alkyl optionally substituted in the aryl radical, $(C_3–C_8)$-cycloalkyl or $(C_3–C_8)$-cycloalkyl-$(C_1–C_8)$-alkyl;

$R^{14a}$ is optionally substituted heteroaryl, heteroaryl-$(C_1–C_8)$-alkyl optionally substituted in the heteroaryl radical, or $R^{15}$;

$R^{14b}$ and $R^{14d}$ independently of one another are $(C_6–C_{14})$-aryl-$(C_1–C_8)$-alkyl optionally substituted in the aryl radical, optionally substituted heteroaryl, heteroaryl-$(C_1–C_8)$-alkyl optionally substituted in the heteroaryl radical, or $R^{15}$;

$R^{14c}$ and $R^{14e}$ independently of one another are $(C_1–C_{18})$-alkyl, optionally substituted $(C_6–C_{14})$-aryl, $(C_6–C_{14})$-aryl-$(C_1–C_8)$-alkyl which can also be substituted in the aryl radical, optionally substituted heteroaryl, heteroaryl-$(C_1–C_8)$-alkyl optionally substituted in the heteroaryl radical, or the radical $R^{15}$;

$R^{14f}$ is $(C_6–C_{14})$-aryl-$(C_1–C_8)$-alkyl optionally substituted in the aryl radical, optionally substituted heteroaryl, heteroaryl-$(C_1–C_8)$-alkyl optionally substituted in the heteroaryl radical, $(C_9–C_{12})$-cycloalkyl-$(C_1–C_8)$-alkyl, $(C_6–C_{12})$-bicycloalkyl, $(C_6–C_{12})$-bicycloalkyl-$(C_1–C_8)$-alkyl, $(C_6–C_{12})$-tricycloalkyl or $(C_6–C_{12})$-tricycloalkyl-$(C_1–C_8)$-alkyl;

$R^{15}$ is $R^{16}$-$(C_1–C_6)$-alkyl or $R^{16}$;

$R^{16}$ is the radical of a 3-membered to 12-membered monocyclic ring or the radical of a 6-membered to 24-membered bicyclic or tricyclic ring, where these rings are saturated or partially unsaturated and can also contain one, two, three or four identical or different ring heteroatoms from the group consisting of nitrogen, oxygen and sulfur and can also be substituted by one or more identical or different substituents from the group consisting of $(C_1–C_4)$-alkyl and oxo;

Het is the radical of a 5-membered to 10-membered monocyclic or polycyclic heterocycle bonded via a ring nitrogen atom, which can be aromatic or partially unsaturated or saturated and can contain one, two, three or four identical or different additional ring heteroatoms selected from the group consisting of oxygen, nitrogen and sulfur and which can optionally be substituted on carbon atoms and additional ring nitrogen atoms, it being possible for substituents on additional ring nitrogen atoms to be identical or different radicals $R^c$, $R^cCO$ or $R^cO$—CO;

g and h independently of one another are 0 or 1;

in all their stereoisomeric forms and mixtures thereof in all ratios, and their physiologically tolerable salts.

DESCRIPTION OF PREFERRED EMBODIMENT

Alkyl radicals in the inventive compounds can be straight-chain or branched. This also applies if they carry substituents or occur as substituents of other radicals, for example in alkoxy radicals, alkoxycarbonyl radicals, or arylalkyl radicals. The same applies to divalent alkylene radicals. Examples of suitable $(C_1–C_{18})$-alkyl radicals are: methyl, ethyl, n-propyl, n-butyl, n-pentyl, n-hexyl, heptyl, octyl, decyl, undecyl, dodecyl, tridecyl, pentadecyl, hexadecyl, heptadecyl, octadecyl, isopropyl, isobutyl, isopentyl, isohexyl, 3-methylpentyl, 2,3,5-trimethylhexyl, sec-butyl, tert-butyl, tert-pentyl, neopentyl. Preferred alkyl radicals are methyl, ethyl, n-propyl, isopropyl, n-butyl, isobutyl, sec-butyl, tert-butyl. The two free bonds in an alkylene radical can start from the same carbon atom or start from different carbon atoms. Examples of alkylene radicals are methylene, ethylene (=1,2-ethylene), tri-, tetra-, penta- and hexamethylene, 1-methylethylene and 2-methylethylene (=1,2-propylene), 1,1-dimethylethylene, 2,2-dimethyl-1,3-propylene, methylene substituted by an alkyl radical, for example methylene which is substituted by a methyl group (=methylmethylene or 1,1-ethylene or ethylidene), methylene which is substituted by an ethyl group, an isopropyl group, an isobutyl group or a tert-butyl group, or methylene which is substituted by two alkyl radicals, for example dimethylmethylene (=2,2-propylene or 2-propylidene).

Alkenyl radicals and alkenylene radicals as well as alkynyl radicals can also be straight-chain or branched. Examples of alkenyl radicals are vinyl, 1-propenyl, 2-propenyl (=allyl), butenyl, 3-methyl-2-butenyl, examples of alkenylene radicals are vinylene or propenylene. Examples of alkynyl radicals are ethynyl, 1-propynyl, 2-propynyl (=propargyl) or 6-hexynyl.

Examples of cycloalkyl radicals are, in particular, cyclopropyl, cyclobutyl, cyclopentyl, cyclohexyl, cycloheptyl, cyclooctyl, cyclononyl, cyclodecyl, cycloundecyl and cyclododecyl, which can also be substituted, for example, by $(C_1–C_4)$-alkyl. Examples of substituted cycloalkyl radicals which may be mentioned are 4-methylcyclohexyl and 2,3-dimethylcyclopentyl. The same examples and substituents applies analogously to cycloalkylene radicals.

If $R^{16}$ is the radical of a saturated monocyclic ring which contains no ring heteroatoms, it is a cycloalkyl radical, if the radical $R^{16}$ contains one or more heteroatoms in the ring, it is a heterocyclic radical. The 3-membered to 12-membered rings can contain 3, 4, 5, 6, 7, 8, 9, 10, 11 or 12 ring members. Bicycloalkyl radicals, tricycloalkyl radicals and the radicals of 6-membered to 24-membered bicyclic and tricyclic rings representing $R^{16}$ are formally obtained by abstraction of a hydrogen atom from bicycles or tricycles. As ring members, the basic bicycles and tricycles can either contain only carbon atoms, they can thus be bicycloalkanes or tricycloalkanes, or in the case of the radicals representing $R^{16}$ they can also contain one to four identical or different heteroatoms selected from the group of nitrogen, oxygen and sulfur, they can thus be aza-, oxa- and thiabicyclo- and -tricycloalkanes. If heteroatoms are contained, preferably one or two heteroatoms, in particular nitrogen atoms or oxygen atoms, are contained. This also applies to the 3-membered to 12-membered monocyclic rings. The heteroatoms can occupy any desired positions in the bicyclic or tricyclic structure; they can be located in the bridges or, in the case of nitrogen atoms, also on the bridgeheads. Both the bicycloalkanes and tricycloalkanes and their heteroanalogs can be completely saturated or can contain one or more double bonds; preferably they contain one or two double bonds or are, in particular, completely saturated. Both the bicycloalkanes and tricycloalkanes as well as the heteroanalogs and both the saturated and the unsaturated representatives can be unsubstituted or can be substituted in any desired suitable positions by one or more identical or different substituents, for example one or two oxo groups and/or in particular by one or more, for example, one, two, three or four, identical or different $(C_1–C_4)$-alkyl groups, for example methyl groups or isopropyl groups, preferably methyl groups. The free bond of the bicyclic or tricyclic radical can be located in any desired position of the molecule, the radical can thus be bonded via a bridgehead atom or an atom in a bridge. The free bond can also be located in any desired stereochemical position, for example in an exo position or an endo position. The same in turn applies to the monocyclic rings.

Examples of parent structures of bicyclic ring systems, from which a bicycloalkyl radical or a bicyclic radical representing $R^{16}$ can be derived, are norbornane (=bicyclo[2.2.1]heptane), bicyclo[2.2.2]octane and bicyclo[3.2.1]octane, examples of heteroatom-containing, of unsaturated or of substituted ring systems are 7-azabicyclo[2.2.1]heptane, bicyclo[2.2.2]oct-5-ene and camphor (=1,7,7-trimethyl-2-oxobicyclo[2.2.1]heptane).

Examples of systems from which a tricycloalkyl radical or a tricyclic radical representing $R^{16}$ can be derived are twistane (=tricyclo[4.4.0.0$^{3,8}$]decane), adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane.

Preferably, bicycloalkyl radicals, tricycloalkyl radicals and bicyclic or tricyclic radicals representing $R^{16}$ are derived from bridged bicycles or tricycles, i.e., from systems in which rings have two or more than two atoms in common. Furthermore preferred in the radicals representing $R^{16}$ are bicyclic or tricyclic radicals having 6 to 18 ring members, particularly preferably those having 7 to 12 ring members. Specifically, additionally preferred radicals are the 2-norbornyl radical, both that having the free bond in the exo position and that having the free bond in the endo position, the 2-bicyclo[3.2.1]octyl radical, the 1-adamantyl radical, the 2-adamantyl radical, the noradamantyl radical, for example the 3-noradamantyl radical, and the homoadamantyl radical. The 1- and the 2-adamantyl radical are especially preferred.

($C_6$–$C_{14}$)-Aryl groups are, for example, phenyl, 1-naphthyl, 2-naphthyl, biphenylyl, anthryl or fluorenyl, ($C_6$–$C_{12}$)-aryl groups are, for example, phenyl, naphthyl or biphenylyl, ($C_6$–$C_{10}$)-aryl groups are, for example, phenyl or naphthyl. Preferred aryl radicals are in particular 2-biphenylyl, 3-biphenylyl, 4-biphenylyl, 1-naphthyl, 2-naphthyl and in particular phenyl. Aryl radicals, in particular phenyl radicals, can be monosubstituted or polysubstituted, preferably monosubstituted, disubstituted or trisubstituted, by identical or different radicals selected from the group of ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, amino, trifluoromethyl, hydroxyl, methylenedioxy, ethylenedioxy, cyano, hydroxycarbonyl, aminocarbonyl, ($C_1$–$C_4$)-alkoxycarbonyl, phenyl, phenoxy, benzyl, benzyloxy, ($R^d$O)$_2$p(O), ($R^d$O)$_2$P(O)—O—, or tetrazolyl. The same applies, for example, to radicals such as arylalkyl or arylcarbonyl. Arylalkyl radicals are, in particular, benzyl as well as 1- and 2-naphthylmethyl, 2-, 3- and 4-biphenylylmethyl and 9-fluorenylmethyl, and also 1-phenylethyl and 2-phenylethyl, all of which can also be substituted.

Substituted arylalkyl radicals are, for example, benzyl and naphthylmethyl substituted in the aryl moiety by one or more ($C_1$–$C_8$)-alkyl radicals, in particular ($C_1$–$C_4$)-alkyl radicals, for example 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7- and 8-methyl-1-naphthylmethyl, 1-, 3-, 4-, 5-, 6-, 7- and 8-methyl-2-naphthylmethyl, benzyl and naphthylmethyl substituted in the aryl moiety by one or more ($C_1$–$C_8$)-alkoxy radicals, in particular ($C_1$–$C_4$)-alkoxy radicals, for example 4-methoxybenzyl, 4-neopentyloxybenzyl, 3,5-dimethoxybenzyl, 3,4-methylenedioxybenzyl, 2,3,4-trimethoxybenzyl, 2-, 3- and 4-nitrobenzyl, halobenzyl, for example 2-, 3- and 4-chlorobenzyl and 2-, 3- and 4-fluorobenzyl, 3,4-dichlorobenzyl, pentafluorobenzyl, trifluoromethylbenzyl, for example 3- and 4-trifluoromethylbenzyl or 3,5-bis(trifluoromethyl)benzyl. Substituted arylalkyl radicals, however, can also have different substituents. The substituted aryl radicals contained in the substituted arylalkyl radicals mentioned by way of example are at the same time examples of substituted aryl radicals.

In monosubstituted phenyl radicals, the substituent can be located in the 2-position, the 3-position or the 4-position, the 3-position and the 4-position being preferred. If phenyl is disubstituted, the substituents can be located in the 2,3-position, 2,4-position, 2,5-position, 2,6-position, 3,4-position or 3,5-position. Preferably, in disubstituted phenyl radicals the two substituents are arranged in the 3,4-position. If phenyl is trisubstituted, the substituents can be located, for example, in the 2,3,4-position, 2,3,5-position, 2,3,6-position, 2,4,5-position, 2,4,6-position or 3,4,5-position.

The same applies to substituted phenylene radicals. Phenylene radicals can be present, for example, as 1,4-phenylene or as 1,3-phenylene.

Phenylene-($C_1$–$C_6$)-alkyl is, in particular, phenylenemethyl and phenyleneethyl. Phenylene-($C_2$–$C_6$)-alkenyl is, in particular, phenyleneethenyl and phenylenepropenyl.

Examples of heterocyclic parent structures from which heteroaryl radicals, 5-membered or 6-membered heterocycles, mono- or bicyclic 5-membered to 12-membered heterocyclic rings, 3-membered to 12-membered monocyclic rings and 6-membered to 24-membered bicyclic and tricyclic rings containing one or more ring heteroatoms and 5-membered to 10-membered monocyclic or polycyclic heterocycles can be derived, are pyrrole, furan, thiophene, imidazole, pyrazole, oxazole, isoxazole, thiazole, isothiazole, tetrazole, pyran, thiopyran, pyridine, pyrazine, pyrimidine, indole, isoindole, indazole, chroman, phthalazine, quinoline, isoquinoline, quinoxaline, quinazoline, cinnoline, azepine, or benzo-fused, cyclopenta-, cyclohexa- or cyclohepta-fused derivatives of these heterocycles. The radicals can be bonded in any desired positions. The heterocycles can in each case be present in maximally unsaturated form or partially saturated form (=partially unsaturated form), for example in the dihydro form or tetrahydro form, or in completely saturated form (perhydro form). If not stated otherwise, the heterocycles can be substituted, for example, on one or more nitrogen atoms by ($C_1$–$C_7$)-alkyl, for example methyl or ethyl, phenyl or phenyl-($C_1$–$C_4$)-alkyl, for example benzyl, and/or on one or more carbon atoms by ($C_1$–$C_4$)-alkyl, halogen, hydroxyl, ($C_1$–$C_4$)-alkoxy, for example methoxy, phenyl-($C_1$–$C_4$)-alkoxy, for example benzyloxy, or oxo. Nitrogen heterocycles can also be present as N-oxides.

In particular, a heteroaryl radical is derived from a 5-membered to 12-membered heterocycle containing one or more aromatic rings, which can contain one, two, three or four identical or different heteroatoms selected from the group of nitrogen, oxygen and sulfur. It is preferably derived from a 5-membered to 10-membered heterocycle, i.e., from a 5-, 6-, 7-, 8-, 9- or 10-membered heterocycle, particularly preferably from a 5-membered to 6-membered heterocycle. It preferably contains one, two or three heteroatoms, particularly preferably one or two. Examples of heteroaryl radicals are pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, or a benzo-fused, cyclopenta-, cyclohexa- or cyclohepta-fused derivative of these radicals. Heteroaryl radicals can be monosubstituted or polysubstituted, preferably monosubstituted, disubstituted or trisubstituted, by identical or different radicals selected from the group of $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, methylenedioxy, ethylenedioxy, cyano, hydroxycarbonyl, aminocarbonyl, $(C_1-C_4)$-alkoxycarbonyl, phenyl, phenoxy, benzyl, benzyloxy, $(R^dO)_2P(O)$, $(R^dO)_2P(O)$—O—, or tetrazolyl.

Heteroaryl radicals of this type are, for example, 1-pyrrolyl, 2-pyrrolyl, 3-pyrrolyl, phenylpyrrolyl such as, for example, 4- or 5-phenyl-2-pyrrolyl, 2-furyl, 3-furyl, 2-thienyl, 3-thienyl, 1-imidazolyl, 2-imidazolyl, 4-imidazolyl, 5-imidazolyl, methylimidazolyl such as, for example, 1-methyl-2-, 4- or -5-imidazolyl, 1,3-thiazol-2-yl, 1-tetrazolyl, 5-tetrazolyl, 2-pyridyl, 3-pyridyl, 4-pyridyl, N-oxido-2-, 3- or 4-pyridyl, 2-pyrazinyl, 2-pyrimidinyl, 4-pyrimidinyl, 5-pyrimidinyl, 2-indolyl, 3-indolyl, 5-indolyl, substituted 2-indolyl such as, for example, 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-quinolyl, 3-quinolyl or 4-quinolyl, 1-isoquinolyl, 3-isoquinolyl or 4-isoquinolyl, 1-hydroxy-3-isoquinolyl (=1-oxo-1,2-dihydro-3-isoquinolyl), 2-quinoxalinyl, 2-benzofuranyl, 2-benzothienyl, 2-benzoxazolyl or 2-benzothiazolyl.

Radicals of partly hydrogenated or completely hydrogenated heterocyclic rings are, for example, dihydropyridinyl, tetrahydropyridinyl, pyrrolidinyl, for example 2-, 3- or 4-(N-methylpyrrolidinyl), piperidinyl, piperazinyl, morpholinyl, thiomorpholinyl, tetrahydrothienyl, benzodioxolan-2-yl.

Heterocyclic radicals representing the radical Het can be unsubstituted on carbon atoms and/or ring nitrogen atoms or monosubstituted or polysubstituted, for example, disubstituted, trisubstituted, tetrasubstituted or pentasubstituted, by identical or different substituents. Carbon atoms can be substituted, for example, by $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, oxo, methylenedioxy, cyano, hydroxycarbonyl, aminocarbonyl, $(C_1-C_4)$-alkoxycarbonyl, phenyl, phenoxy, benzyl, benzyloxy, $(R^dO)_2P(O)$, $(R^dO)_2P(O)$—O—, tetrazolyl. Sulfur atoms can be oxidized to the sulfoxide or to the sulfone. Examples of the radical Het are 1-pyrrolyl, 1-imidazolyl, 1-pyrazolyl, 1-tetrazolyl, dihydropyridin-1-yl, tetrahydropyridin-1-yl, 1-pyrrolidinyl, 1-piperidinyl, 1-piperazinyl, 4-substituted 1-piperazinyl, 4-morpholinyl, 4-thiomorpholinyl, 1-oxo-4-thiomorpholinyl, 1,1-dioxo-4-thiomorpholinyl, perhydroazepin-1-yl, 2,5-dimethyl-1-pyrrolyl, 2,6-dimethyl-1-piperidinyl, 3,3-dimethyl-4-morpholinyl, 4-isopropyl-2,2,6,6-tetramethyl-1-piperazinyl.

Halogen is fluorine, chlorine, bromine or iodine, in particular fluorine or chlorine.

The divalent alkylene radical representing $R^4$, which is substituted by a radical selected from the group of $R^{11}NH$, $(C_9-C_{12})$-cycloalkyl, $(C_9-C_{12})$-cycloalkyl-$(C_1-C_8)$, $(C_1-C_8)$-bicycloalkyl , $(C_6-C_{12})$-bicycloalkyl-$(C_1-C_8)$-alkyl, $(C_6-C_{12})$-tricycloalkyl and $(C_6-C_{12})$-tricycloalkyl-$(C_1-C_8)$-alkyl, can be, for example, the radicals —CH$_2$—CH(NHR$^{11}$)— or —CH$_2$—CH$_2$—CH(NHR$^{11}$)—, whose CH(NHR$^{11}$) group is bonded to the radical $E^a$ in the group CO—N(R$^a$)—R$^4$—E$^a$, or the radical —CH$_2$—CH(NHR$^{11}$)—CH$_2$—. Furthermore, the divalent alkylene radical representing $R^4$ can be, for example, the radical —CH(Cy)— or the radical —CH(Cy)—CH$_2$—, whose CH$_2$ group is bonded to the radical $E^a$, where Cy is $(C_9-C_{12})$-cycloalkyl, $(C_9-C_{12})$-cycloalkyl-$(C_1-C_8)$-alkyl, $(C_6-C_{12})$-bicycloalkyl, $(C_1-C_8)$-bicycloalkyl-$(C_1-C_8)$-alkyl, $(C_1-C_8)$-tricycloalkyl or $(C_6-C_{12})$-tricycloalkyl-$(C_1-C_8)$-alkyl. In all these radicals mentioned by way of example, however, alkyl radicals, for example methyl radicals, can also be contained instead of one or two of the hydrogen atoms indicated.

The divalent radical of an amino acid, imino acid or azaamino acid which represents $R^5$ or $R^6$ is obtained from the corresponding amino acid, imino acid or azaamino acid as customary in peptide chemistry by formally removing a hydrogen atom from its N-terminal amino group or from the imino group and removing the hydroxyl group from the C-terminal carboxylic acid group. By means of the free bond thus formed on the amino group or the imino group, this group is then linked to the carbonyl group of the neighboring group through an amide bond, the N-terminal amino group or imino group contained in $R^5$ being bonded to the CO group in the group CO—$R^5$—$R^6$—$R^7$. Correspondingly, the carbonyl group formally formed from the carboxylic acid group by the removal of the hydroxyl group is linked by means of its free bond to a nitrogen atom of the neighboring group $R^6$ or $R^7$ through an amide bond. As indicated above, the nitrogen atoms of the amide bonds, i.e., the groups CO—N(R$^b$), through which the CO group in the group CO—$R^5$—$R^6$—$R^7$ is linked to the group $R^5$ and through which the groups $R^5$ and $R^6$ are linked to one another, carry the substituent $R^b$, which, for example, can be hydrogen or $(C_1-C_4)$-alkyl, for example methyl.

The natural and unnatural amino acids can be present in all stereochemical forms, for example in the D form, the L form or in the form of a mixture of stereoisomers, for example in the form of a racemate. Preferred amino acids are α-amino acids and -amino acids; α-amino acids are particularly preferred. Suitable amino acids, from which $R^5$ and $R^6$ can be derived, are described, for example, in (Houben-Weyl, Methoden der organischen Chemie [Methods of Organic Chemistry], Volume 15/1 and 15/2, Georg Thieme Verlag, Stuttgart, 1974), and include Aad, Abu, γuba, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid, 2-(p-chlorophenyl)-aminoacetic acid.

If $R^5$ and/or $R^6$ is the radical of a natural or unnatural α-amino acid which carries a hydrogen atom on the α-carbon atom, then the divalent radical —N(R$^b$)—CH(SC)—CO— is present, in which SC is the side chain of the α-amino acid, i.e., for example, one of the substituents which are contained in the α-position of the abovementioned α-amino acids which are unbranched in the α-position. Examples of side chains are alkyl radicals, for example the methyl group in alanine or the isopropyl group in valine, the benzyl radical in phenylalanine, the phenyl radical in phenylglycine, the 4-aminobutyl radical in lysine or the hydroxycarbonylmethyl group in aspartic acid. Apart from by their chemical structure, such side chains and thus the amino acids can also be arranged in groups within the meaning of the present invention on the basis of their physicochemical properties, for example lipophilic side chains can be differentiated from hydrophilic side chains which contain polar groups. Examples of lipophilic side chains which can be contained in amino acids representing $R^5$ and/or $R^6$ are alkyl radicals, arylalkyl radicals or aryl radicals, for example $(C_1–C_6)$-alkyl radicals, $(C_6–C_{12})$-aryl-$(C_1–C_4)$-alkyl radicals optionally substituted in the aryl radical and optionally substituted $(C_1–C_8)$-aryl radicals, where the above explanations apply to these radicals.

Azaamino acids are natural or unnatural amino acids in which a CH unit is replaced by a nitrogen atom, for example in a-amino acids the central structural unit

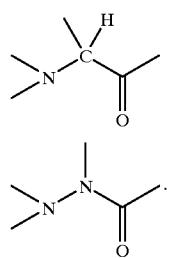

Suitable radicals of imino acids are, in particular, radicals of heterocycles selected from the following group: pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid, hydroxypyrrolidine-2-carboxylic acid, all of which can optionally be substituted (see following formulae):

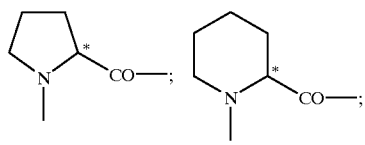

-continued

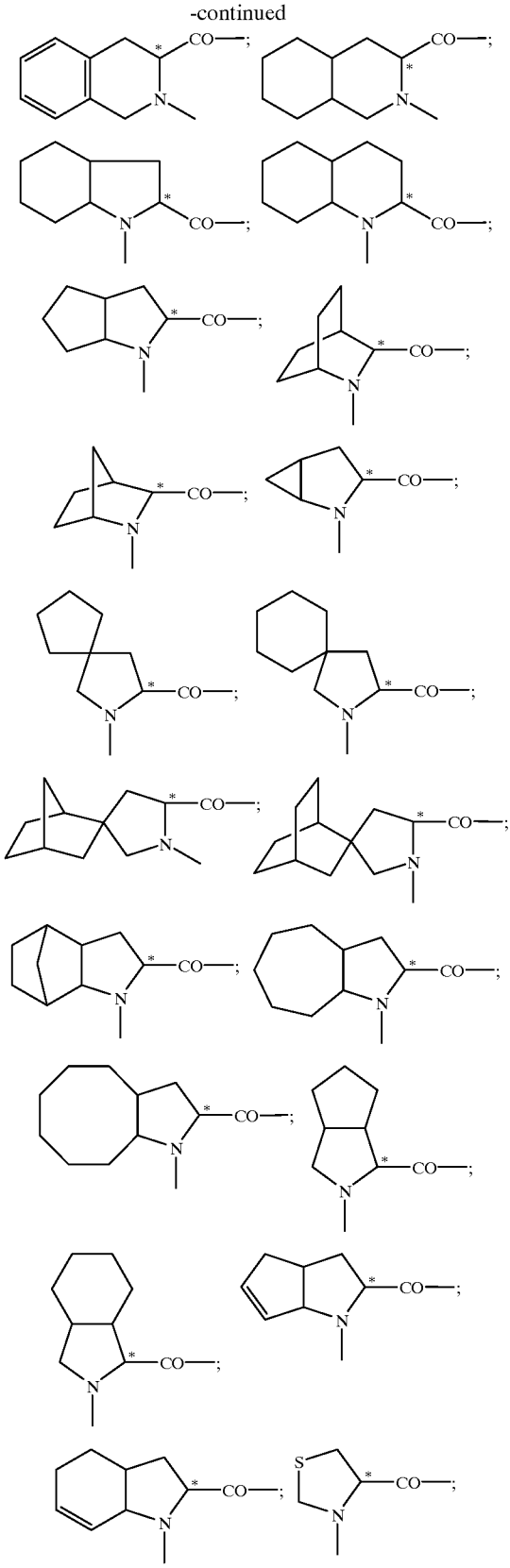

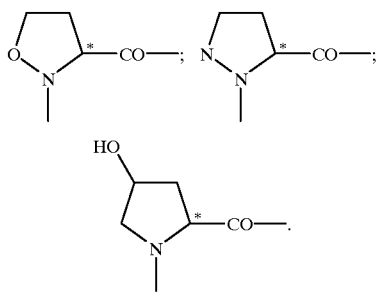

The heterocycles on which the radicals mentioned are based are disclosed, for example, in U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Acid groups in natural or unnatural amino acids, imino acids and azaamino acids can also be present as esters or amides, for example as $(C_1-C_4)$-alkyl esters such as, for example, as methyl esters, ethyl esters, isopropyl esters, isobutyl esters or tert-butyl esters, benzyl esters, unsubstituted amides, methylamides, ethylamides, semicarbazides or ω-amino-$(C_2-C_8)$-alkylamides.

Functional groups of the amino acids, imino acids and azaamino acids can be present in protected form. Suitable protective groups such as, for example, urethane protective groups, carboxyl protective groups and side chain protective groups are described in Hubbuch, Kontakte (Merck) 1979, No. 3, pages 14 to 23, and in Bullesbach, Kontakte (Merck) 1980, No.1, pages 23 to 35. The following may be mentioned in particular: Aloc, Pyoc, Fmoc, Tcboc, Z, Boc, Ddz, Bpoc, Adoc, Msc, Moc, Z($NO_2$), Z($Hal_n$), Bobz, Iboc, Adpoc, Mboc, Acm, tert-butyl, OBzl, ONbzl, OMbzl, Bzl, Mob, Pic, Trt.

The compounds of the formula I can be present in stereoisomeric forms. If the compounds of the formula I contain one or more centers of asymmetry, these can independently of one another have the S configuration or the R configuration. The invention includes all possible stereoisomers, for example enantiomers and diastereomers, and mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. In the presence of cis/trans isomerism, the invention relates to both the cis form and the trans form and mixtures of these forms. Individual stereoisomers can be prepared, if desired, by separation of a mixture according to customary methods, for example by chromatography or crystallization, by use of stereochemically homogeneous starting substances in the synthesis or by stereoselective synthesis. If appropriate, derivatization using a chiral reagent can be carried out before separation of stereoisomers and the diastereomeric compounds obtained can then be separated according to customary methods, for example by crystallization or chromatography. A stereoisomer mixture can be separated at the stage of the compounds of the formula I or at the stage of an intermediate in the course of the synthesis.

In the presence of mobile hydrogen atoms, the present invention also includes all tautomeric forms of the compounds of the formula I, for example lactam/lactim tautomers.

If the compounds of the formula I contain one or more acidic or basic groups, the invention also relates to the corresponding physiologically or toxicologically tolerable salts, in particular the pharmaceutically utilizable salts. Thus the compounds of the formula I which contain one or more acidic groups, for example carboxylic acid groups or sulfonic acid groups, can be present on these groups and be used according to the invention, for example, as alkali metal salts, alkaline earth metal salts or ammonium salts. Examples of such salts are sodium salts, potassium salts, calcium salts, magnesium salts or salts with ammonia or organic amines such as, for example, ethylamine, ethanolamine, triethanolamine or amino acids.

Compounds of the formula I which contain one or more basic, i.e., protonatable, groups, for example amino groups, amidino groups or guanidino groups, can be present and be used according to the invention in the form of their acid addition salts with inorganic or organic acids, for example, as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc. If the compounds of the formula I simultaneously contain acidic and basic groups in the molecule, the invention also includes internal salts or betaines in addition to the salt forms described.

Salts can be obtained from the compounds of the formula I according to customary procedures known to the person skilled in the art, for example by combining with an organic or inorganic acid or base in a solvent or dispersant, or alternatively from other salts by anion exchange or cation exchange. The present invention also includes all salts of the compounds of the formula I which are not directly suitable for use in pharmaceuticals because of low physiological tolerability, but are suitable, for example, as intermediates for chemical reactions or for the preparation of physiologically tolerable salts.

The present invention furthermore includes all solvates of compounds of the formula I, for example hydrates or adducts with alcohols, as well as derivatives of the compounds of the formula I, for example esters, pro-drugs and active metabolites.

The individual structural elements in the formula I preferably have the following meanings.

W is preferably $R^1$—A—$C(R^{13})$.

A is preferably methylene, ethylene, trimethylene, tetramethylene, pentamethylene, cyclohexylene, phenylene, phenylenemethyl or phenyleneethyl.

Y is preferably a carbonyl group.

Z is preferably $N(R^0)$.

B is preferably the divalent methylene radical or ethylene radical (=1,2-ethylene), in particular a methylene radical, where each of the radicals can be unsubstituted or substituted. Particularly preferably, both radicals are substituted. If a divalent methylene or ethylene radical (=1,2-ethylene) -representing B is substituted, it is preferably substituted by a radical selected from the group of $(C_1-C_8)$-alkyl, $(C_2-C_6)$-alkenyl, $(C_2-C_6)$-alkynyl, $(C_3-C_8)$-cycloalkyl, in particular $(C_5-C_6)$-cycloalkyl, $(C_3-C_8)$-cycloalkyl-$(C_1-C_4)$-alkyl, in particular $(C_5-C_6)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl and heteroaryl-$(C_1-C_4)$-alkyl optionally substituted in the heteroaryl radical. It is particularly preferably substituted by a radical selected from the group of $(C_1-C_8)$-alkyl, in particular $(C_1C_6)$-alkyl, $(C_5-C_6)$-cycloalkyl, $(C_5-C_6)$-cycloalkyl-$(C_1-C_4)$-alkyl, phenyl, benzyl and phenylethyl; it is very particularly preferably substituted by a $(C_1-C_6)$-alkyl radical, i.e., a straight-chain or branched alkyl radical having 1, 2, 3, 4, 5, 6, 7 or 8 carbon atoms, in particular by a $(C_1-C_6)$-alkyl radical.

E and $E^a$ preferably independently of one another are $R^{10}CO$.

R, $R^a$ and $R^b$ preferably independently of one another are hydrogen, $(C_1-C_6)$-alkyl or benzyl, in particular hydrogen, methyl or ethyl.

$R^c$ is preferably hydrogen, $(C_1-C_6)$-alkyl, $(C_5-C_6)$-cycloalkyl, $(C_5-C_6)$-cycloalkyl-$(C_1-C_2)$-alkyl, optionally substituted phenyl or phenyl-$(C_1-C_2)$-alkyl optionally substituted in the phenyl radical.

$R^0$ is preferably hydrogen, $(C_1-C_8)$-alkyl, $(C_3-C_{10})$-cycloalkyl, $(C_3-C_{10})$-cycloalkyl-$(C_1-C_6)$-alkyl, $(C_6-C_{12})$-bicycloalkyl, $(C_1-C_8)$-bicycloalkyl-$(C_1-C_6)$-alkyl, $(C_6-C_{12})$-tricycloalkyl, $(C_1-C_8)$-tricycloalkyl-$(C_1-C_6)$-alkyl, optionally substituted $(C_6-C_{12})$-aryl, $(C_1-C_8)$-aryl-$(C_1-C_6)$-alkyl optionally substituted in the aryl radical, optionally substituted heteroaryl, heteroaryl-$(C_1-C_6)$-alkyl optionally substituted in the heteroaryl radical, $(C_1-C_8)$-alkyl—CO, $(C_3-C_{10})$-cycloalkyl—CO, $(C_3-C_{10})$-cycloalkyl-$(C_1-C_6)$-alkyl—CO, $(C_6-C_{12})$-bicycloalkyl—CO, $(C_1-C_8)$-bicycloalkyl-$(C_1-C_6)$-alkyl—CO, $(C_6-C_{12})$-tricycloalkyl-CO, $(C_6-C_{12})$-tricycloalkyl-$(C_1-C_6)$-alkyl—CO, optionally substituted $(C_1-C_8)$-aryl—CO, $(C_1-C_8)$-aryl-$(C_1-C_6)$-alkyl—CO optionally substituted in the aryl radical, optionally substituted heteroaryl—CO, heteroaryl-$(C_1-C_6)$-alkyl—CO optionally substituted in the heteroaryl radical, $(C_1-C_8)$-alkyl-S(O)$_n$, $(C_3-C_{10})$-cycloalkyl-S(O)$_n$, $(C_3-C_{10})$-cycloalkyl-$(C_1-C_6)$-alkyl-S(O)$_n$, $(C_1-C_8)$-bicycloalkyl-S(O)$_n$, $(C_1-C_8)$-bicycloalkyl-$(C_1-C_6)$-alkyl-S(O)$_n$, $(C_6-C_{12})$-tricycloalkyl-S(O)$_n$, $(C_6-C_{12})$-tricycloalkyl-$(C_1-C_6)$-alkyl-S(O)$_n$, optionally substituted $(C_1-C_8)$-aryl-S(O)$_n$, $(C_1-C_8)$-aryl-$(C_1-C_6)$-alkyl-S(O)$_n$, optionally substituted in the aryl radical, optionally substituted heteroaryl-S(O)$_n$ or heteroaryl-$(C_1-C_6)$-alkyl-S(O)$_n$ optionally substituted in the heteroaryl radical, where n is 1 or 2.

Particularly preferably, $R^0$ is $(C_1-C_8)$-alkyl, $(C_3-C_{10})$-cycloalkyl, $(C_3-C_{10})$-cycloalkyl-$(C_1-C_6)$-alkyl, $(C_1-C_8)$-bicycloalkyl, $(C_1-C_8)$-bicycloalkyl-$(C_1-C_6)$-alkyl, $(C_6-C_{12})$-tricycloalkyl, $(C_1-C_8)$-tricycloalkyl-$(C_1-C_6)$-alkyl, optionally substituted $(C_1-C_8)$-aryl, $(C_1-C_8)$-aryl-$(C_1-C_6)$-alkyl optionally substituted in the aryl radical, optionally substituted heteroaryl or heteroaryl-$(C_1-C_6)$-alkyl optionally substituted in the heteroaryl radical, very particularly preferably $(C_6-C_{12})$-aryl-$(C_1-C_4)$-alkyl optionally substituted in the aryl radical or heteroaryl-$(C_1-C_4)$-alkyl optionally substituted in the heteroaryl radical, additionally preferably $(C_6-C_{12})$-aryl-$(C_1-C_4)$-alkyl optionally substituted in the aryl radical, in particular $(C_6-C_{12})$-aryl-$(C_1-C_2)$-alkyl which is unsubstituted or monosubstituted or polysubstituted in the aryl radical.

$R^1$ is preferably X—NH—C(=NH), X—NH—C(=NX)—NH or X—NH—CH$_2$.

X and $X^1$ are preferably hydrogen, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl or $(C_6-C_{14})$-aryl-$(C_1-C_6)$-alkoxycarbonyl, hydroxyl; $X^1$ is additionally R'—NH—C(=N—R''), where R' and R'' independently of one another have the preferred meanings of X.

$R^2$, $R^{2a}$ and $R^{2b}$ preferably independently of one another are hydrogen or $(C_1-C_8)$-alkyl, particularly preferably hydrogen.

$R^3$ is preferably $R^{11}NH$, $(C_{10}-C_{12})$-cycloalkyl, $(C_{10}-C_{12})$-cycloalkyl-$(C_1-C_8)$-alkyl, $(C_7-C_{12})$-bicycloalkyl, $(C_7-C_{12})$-bicycloalkyl-$(C_1-C_8)$-alkyl, $(C_{10}-C_{12})$-tricycloalkyl, $(C_{10}-C_{12})$-tricycloalkyl-$(C_1-C_8)$-alkyl, CO—N($R^a$)—$R^4$—$E^a$ or —CO—$R^5$—$R^6$—Het, particularly preferably $R^{11}NH$, $(C_7-C_{12})$-bicycloalkyl, $(C_7-C_{12})$-bicycloalkyl-$(C_1-C_4)$-alkyl, $(C_{10}-C_{12})$-tricycloalkyl or $(C_{10}-C_{12})$-tricycloalkyl-$(C_1-C_4)$-alkyl, CO—N($R^a$)—$R^4$—$E^a$ or CO—$R^5$—$R^6$—Het, very particularly preferably $R^{11}NH$ or CO—$R^5$—$R^5$-Het.

$R^4$ is preferably a divalent $(C_1-C_4)$-alkylene radical, particularly preferably a $(C_1-C_2)$-alkylene radical which is substituted by a radical selected from the group of $R^{11}NH$, $(C_{10}-C_{12})$-cycloalkyl, $(C_{10}-C_{12})$-cycloalkyl-$(C_1-C_6)$, $(C_7-C_{12})$-bicycloalkyl, $(C_7-C_{12})$-bicycloalkyl-$(C_1-C_6)$-alkyl, $(C_{10}-C_{12})$-tricycloalkyl and $(C_{10}-C_{12})$-tricycloalkyl-$(C_1-C_6)$-alkyl and which can additionally be substituted by one or two identical or different $(C_1-C_4)$-alkyl radicals.

$R^5$ is preferably the divalent radical of a natural or unnatural amino acid, where free functional groups can be protected by protective groups customary in peptide chemistry or can be present as esters or amides, and where the nitrogen atom of the N-terminal amino group carries a radical $R^b$. Particularly preferably, an amino acid representing $R^5$ is an α-amino acid. $R^6$ is preferably a direct bond.

$R^6$ is preferably hydroxyl, $(C_1-C_6)$-alkoxy, $(C_6-C_{10})$-aryl-$(C_1-C_8)$-alkoxy, which can also be substituted in the aryl radical, optionally substituted $(C_6-C_{10})$-aryloxy or $(C_1-C_8)$-alkylcarbonyloxy-$(C_1-C_6)$-alkoxy.

$R^{11}$ is preferably $R^{12}NH$—CO, $R^{14a}O$—Co, $R^{14b}CO$, $R^{14c14d}S(O)_2$.

$R^{12}$ is preferably optionally substituted $(C_6-C_{14})$-aryl, $(C_6-C_{14})$-aryl-$(C_1-C_8)$-alkyl which can also be substituted in the aryl radical, optionally substituted heteroaryl, heteroaryl-$(C_1-C_8)$-alkyl optionally substituted in the heteroaryl radical, or the radical $R^{15}$.

$R^{13}$ is preferably hydrogen, $(C_1-C_6)$-alkyl, $(C_3-C_8)$-cycloalkyl or benzyl, particularly preferably $(C_1-C_6)$-alkyl, $(C_3-C_8)$-cycloalkyl or benzyl, where a very particularly preferred alkyl radical which $R^{13}$ represents is the methyl radical.

$R^{14a}$ is preferably heteroaryl-$(C_1-C_2)$-alkyl optionally substituted in the heteroaryl radical, or the radical $R^{15}$, particularly preferably the radical $R^{15}$.

$R^{14b}$ and $R^{14d}$ are preferably independently of one another $(C_6-C_{10})$-aryl-$(C_1-C_4)$-alkyl optionally substituted in the aryl radical, heteroaryl-$(C_1-C_4)$-alkyl optionally substituted in the heteroaryl radical, or the radical $R^{15}$.

$R^{14c}$ is preferably $(C_1-C_{10})$-alkyl, $(C_6-C_{10})$-aryl-$(C_1-C_4)$-alkyl which can also be substituted in the aryl radical, heteroaryl-$(C_1-C_4)$-alkyl optionally substituted in the heteroaryl radical, or the radical $R^{15}$.

$R^{14a}$ is preferably $(C_1-C10)$-alkyl, optionally substituted $(C_6-C_{14})$-aryl, $(C_6-C_{14})$-aryl-$(C_1-C_8)$-alkyl which can also be substituted in the aryl radical, or the radical $R^{15}$.

$R^{14f}$ is preferably $(C_6-C_{14})$-aryl-$(C_1-C_8)$-alkyl optionally substituted in the aryl radical, $(C_9-C_{12})$-cycloalkyl-$(C_1-C_8)$-alkyl, $(C_1-C_8)$-bicycloalkyl, $(C_6-C_{12})$-bicycloalkyl-$(C_1-C_8)$-alkyl, $(C_6-C_{12})$-tricycloalkyl or $(C_1-C_8)$-tricycloalkyl-$(C_1-C_8)$-alkyl.

$R^{15}$ is preferably $R^{16}$—$(C_1-C_3)$-alkyl or $R^{16}$, particularly preferably $R^{16}$—$(C_1)$-alkyl or $R^{16}$.

$R^{16}$ is preferably the radical of a 5-membered to 10-membered monocyclic ring or the radical of a 6-membered to 14-membered bicyclic or tricyclic ring, where these rings are saturated or partially unsaturated and can also contain one, two, three or four identical or different ring heteroatoms selected from the group of nitrogen, oxygen and sulfur and can also be substituted by one or more identical or different ($C_1$–$C_4$)-alkyl radicals.

Het is preferably the radical of a 5-membered to 10-membered monocyclic or polycyclic heterocycle bonded via a ring nitrogen atom, which can be aromatic or partially unsaturated or saturated and can contain one or two identical or different additional ring heteroatoms selected from the group of oxygen, nitrogen and sulfur and can be optionally substituted on carbon atoms and ring nitrogen atoms, where identical or different radicals RC, $R^cCO$ or $R^cO$—CO can be substituents on additional ring nitrogen atoms. Particularly preferably, Het is a heterocycle which is saturated and contains no additional ring heteroatom or contains one additional ring heteroatom selected from the group of nitrogen, oxygen and sulfur. If a ring nitrogen atom in the group Het carries a radical $R^cO$—CO, $R^c$ in this radical preferably has a meaning other than hydrogen.

If $R^3$ is $R^{11}NH$, preferably g is 1 and h is 0. If $R^3$ is a cycloalkyl radical, bicycloalkyl radical or tricycloalkyl radical, preferably g is 0 or 1 and h is 1, particularly preferably g is 0 and h is 1. If $R^3$ is CO—N($R^a$)—$R^4$—$E^a$ or CO—$R^5$—$R^6$—$R^7$, preferably g is 0 and h is 1.

Of the compounds of the formula I, those compounds are preferred in which one or more of the radicals have preferred meanings, the present invention relating to all combinations of preferred substituent meanings. Particularly preferred compounds of the formula I are in particular those in which, simultaneously W is $R^1$—A—C($R^{13}$) and therein A is a divalent radical from the group consisting of cyclohexylene, phenylene, phenylenemethyl;

Y is a carbonyl group;

Z is N($R^0$);

B is a divalent methylene radical or ethylene radical (=1,2-ethylene), both radicals being unsubstituted or being substituted by a radical selected from the group of ($C_1$–$C_8$)-alkyl, ($C_3$–$C_8$)-cycloalkyl, ($C_3$–$C_8$)-cycloalkyl-($C_1$–$C_4$)-alkyl, optionally substituted ($C_6$–$C_{10}$)-aryl, ($C_6$–$C_{10}$)-aryl-($C_1$–$C_4$)-alkyl optionally substituted in the aryl radical, optionally substituted heteroaryl and heteroaryl-($C_1$–$C_4$)-alkyl optionally substituted in the heteroaryl radical;

E and $E^a$ independently of one another are $R^{10}CO$;

R, $R^a$ and $R^b$ independently of one another are hydrogen, ($C_1$–$C_6$)-alkyl or benzyl;

$R^c$ is hydrogen, ($C_1$–$C_6$)-alkyl, ($C_5$–$C_6$)-cycloalkyl, ($C_5$–$C_6$)-cycloalkyl-($C_1$–$C_2$)-alkyl, optionally substituted phenyl or phenyl-($C_1$–$C_2$)-alkyl optionally substituted in the phenyl radical;

$R^0$ is ($C_1$–$C_6$)-alkyl, ($C_5$–$C_{10}$)-cycloalkyl, ($C_5$–$C_{10}$)-cycloalkyl-($C_1$–$C_4$)-alkyl, ($C_7$–$C_{12}$)-bicycloalkyl, ($C_7$–$C_{12}$)-bicycloalkyl-($C_1$–$C_4$)-alkyl, ($C_{10}$–$C_{12}$)-tricycloalkyl, ($C_{10}$–$C_{12}$)-tricycloalkyl-($C_1$–$C_4$)-alkyl, optionally substituted ($C_6$–$C_{12}$)-aryl, ($C_6$–$C_{12}$)-aryl-($C_1$–$C_4$)-alkyl optionally substituted in the aryl radical, optionally substituted heteroaryl, heteroaryl-($C_1$–$C_4$)-alkyl optionally substituted in the heteroaryl radical, ($C_1$–$C_6$)-alkyl—CO, ($C_5$–$C_{10}$)-cycloalkyl—CO, ($C_5$–$C_{10}$)-cycloalkyl-($C_1$–$C_4$)-alkyl—CO, ($C_7$–$C_{12}$)-bicycloalkyl—CO, ($C_7$–$C_{12}$)-bicycloalkyl-($C_1$–$C_4$)-alkyl—CO, ($C_{10}$–$C_{12}$)-tricycloalkyl—CO, ($C_{10}$–$C_{12}$)-tricycloalkyl-($C_1$–$C_4$)-alkyl—CO, optionally substituted ($C_6$–$C_{12}$)-aryl—CO, ($C_6$–$C_{12}$)-aryl-($C_1$–$C_4$)-alkyl—CO optionally substituted in the aryl radical, optionally substituted heteroaryl—CO, heteroaryl-($C_1$–$C_4$)-alkyl—CO optionally substituted in the heteroaryl radical, ($C_1$–$C_6$)-alkyl-S(O)$_n$, ($C_5$–$C_{10}$)-cycloalkyl—S(O)$_n$, ($C_5$–$C_{10}$)-cycloalkyl-($C_1$–$C_4$)-alkyl—S(O)$_n$, ($C_7$–$C_{12}$)-bicycloalkyl-S(O)$_n$, ($C_7$–$C_{12}$)-bicycloalkyl-($C_1$–$C_4$)-alkyl-S(O)$_n$, ($C_{10}$–$C_{12}$)-tricycloalkyl-S(O)$_n$, ($C_{10}$–$C_{12}$)-tricycloalkyl-($C_1$–$C_4$)-alkyl-S(O)$_n$, optionally substituted ($C_1$–$C_8$)-aryl-S(O)$_n$, ($C_1$–$C_8$)-aryl-($C_1$–$C_4$)-alkyl-S(O)$_n$, optionally substituted in the aryl radical, optionally substituted heteroaryl—S(O)$_n$ or heteroaryl-($C_1$–$C_4$)-alkyl—S(O)$_n$, optionally substituted in the heteroaryl radical, where n is 1 or 2;

$R^1$ is X—NH—C(=NH), X—NH—C(=NX)—NH or X—NH—CH$_2$;

X is hydrogen, ($C_1$–$C_6$)-alkylcarbonyl, ($C_1$–$C_6$)-alkoxycarbonyl, ($C_1$–$C_8$)-alkylcarbonyloxy-($C_1$–$C_6$)-alkoxycarbonyl, ($C_6$–$C_{14}$)-aryl-($C_1$–$C_6$)-alkoxycarbonyl or hydroxyl;

$R^2$, $R^{2a}$ and $R^{2b}$ independently of one another are hydrogen or ($C_1$–$C_8$)-alkyl;

$R^3$ is $R^{11}NH$, ($C_{10}$–$C_{12}$)-cycloalkyl, ($C_{10}$–$C_{12}$)-Cycloalkyl-($C_1$–$C_4$)-alkyl, ($C_7$–$C_{12}$)-bicycloalkyl, ($C_7$–$C_{12}$)-bicycloalkyl-($C_1$–$C_4$)-alkyl, ($C_{10}$–$C_{12}$)-tricycloalkyl, ($C_{10}$–$C_{12}$)-tricycloalkyl-($C_1$–$C_4$)-alkyl, CO—N($R^a$)—$R^4$—$E^a$ or CO—$R^5$—$R^6$—Het;

$R^{10}$ is hydroxyl, ($C_1$–$C_6$)-alkoxy, ($C_6$–$C_{10}$)-aryl-($C_1$–$C_8$)-alkoxy which can also be substituted in the aryl radical, optionally substituted ($C_6$–$C_{10}$)-aryloxy or ($C_1$–$C_8$)-alkylcarbonyloxy-($C_1$–$C_6$)-alkoxy;

$R^{11}$ is $R^{12}NH$—CO, $R^{14a}O$—CO, $R^{14b}CO$, $R^{14c}S(O)$ or $R^{14d}S(O)_2$;

$R^{14a}$ is heteroaryl-($C_1$–$C_2$)-alkyl optionally substituted in the heteroaryl radical, or the radical $R^{15}$;

$R^{14b}$ and $R^{14d}$ independently of one another are ($C_6$–$C_{10}$)-aryl-($C_1$–$C_2$)-alkyl optionally substituted in the aryl radical, heteroaryl-($C_1$–$C_2$)-alkyl optionally substituted in the heteroaryl radical, or the radical $R^{15}$;

$R^{14c}$ is ($C_1$–$C_6$)-alkyl, ($C_6$–$C_{10}$)-aryl-($C_1$–$C_2$)-alkyl which can also be substituted in the aryl radical, or the radical $R^{15}$;

$R^{15}$ is $R^{16}$—($C_1$–$C_4$)-alkyl or is $R^{16}$;

$R^{16}$ is the radical of a 5-membered to 10-membered monocyclic ring or the radical of a 6-membered to 14-membered bicyclic or tricyclic ring, where these rings are saturated and can also contain one or two identical or different ring heteroatoms selected from the group of nitrogen, oxygen and sulfur and can also be substituted by one, two, three or four identical or different ($C_1$–$C_4$)-alkyl radicals;

Het is the radical of a 5-membered or 10-membered monocyclic heterocycle bonded via a ring nitrogen atom, which can be aromatic or partially unsaturated or saturated and can contain one or two identical or different additional ring heteroatoms selected from the group of oxygen, nitrogen and sulfur and which can optionally be substituted, where substituents on ring nitrogen atoms can be identical or different radicals $R^c$, $R^cCO$ or $R^cO$—CO and there can be one or more identical or different substituents from the group consisting of ($C_1$–$C_6$)-alkyl, ($C_1$–$C_6$)-alkoxy, trifluoromethyl, phenyl and benzyl on carbon atoms; in all their stereoisomeric forms and mixtures thereof in all ratios, and their physiologically tolerable salts.

Very particularly preferred compounds of the formula I are those in which W is $R^1$—A—$C(R^{13})$ and $R^{13}$ is $(C_1-C_6)$-alkyl, $(C_6-C_{14})$-aryl-$(C_1-C_8)$-alkyl optionally substituted in the aryl radical, or $(C_3-C_8)$-cycloalkyl; in all their stereoisomeric forms and mixtures thereof in all ratios, and their physiologically tolerable salts.

Additionally preferred compounds of the formula I are those in which, simultaneously $R^3$ is $R^{11}NH$, $(C_{10}-C_{12})$-cycloalkyl, $(C_{10}-C_{12})$-cycloalkyl-$(C_1-C_4)$-alkyl, $(C_7-C_{12})$-bicycloalkyl, $(C_7-C_{12})$-bicycloalkyl-$(C_1-C_4)$-alkyl, $(C_{10}-C_{12})$-tricycloalkyl, $(C_{10}-C_{12})$-tricycloalkyl-$(C_1-C_4)$-alkyl, CO—$N(R^a)$—$R^4$—$E^a$ or CO—$R^5$—$R^6$—Het;

$R^{11}$ is $R^{15}O$—CO or $R^{15}S(O)_2$;

$R^{15}$ is $R^{16}$—$(C_1-C_3)$-alkyl or $R^{16}$;

$R^{16}$ is the radical of a 5-membered to 6-membered monocyclic ring or the radical of a 6-membered to 12-membered bicyclic or tricyclic ring, where these rings are saturated and can also contain one or two identical or different ring heteroatoms selected from the group of nitrogen and oxygen and can also be substituted by one, two or three identical or different $(C_1-C_4)$-alkyl radicals; in all their stereoisomeric forms and mixtures thereof in all ratios, and their physiologically tolerable salts.

Especially preferred compounds of the formula I are those in which, simultaneously W is $R^1$—A—$C(R^{13})$;

Y is a carbonyl group;

Z is $N(R^0)$;

A is a divalent radical selected from the group of cyclohexylene, phenylene and phenylenemethyl;

B is a divalent methylene radical which is unsubstituted or substituted by a radical selected from the group of $(C_1-C_8)$-alkyl, $(C_5-C_6)$-cycloalkyl, $(C_5-C_6)$-cycloalkyl-$(C_1-C_4)$-alkyl, optionally substituted phenyl, phenyl-$(C_1-C_4)$-alkyl substituted in the phenyl radical, optionally substituted 5-membered or 6-membered heteroaryl and heteroaryl-$(C_1-C_4)$-alkyl optionally substituted in the heteroaryl radical;

E and $E^a$ independently of one another are $R^{10}CO$;

R, $R^a$ and $R^b$ independently of one another are hydrogen or $(C_1-C_4)$-alkyl;

$R^0$ is $(C_1-C_6)$-alkyl, $(C_5-C_6)$-cycloalkyl, $(C_5-C_6)$-cycloalkyl-$(C_1-C_2)$-alkyl, optionally substituted $(C_1-C_8)$-aryl, $(C_1-C_8)$-aryl-$(C_1-C_2)$-alkyl optionally substituted in the aryl radical, optionally substituted heteroaryl, heteroaryl-$(C_1-C_2)$-alkyl optionally substituted in the heteroaryl radical, $(C_1-C_6)$-alkyl-CO, $(C_5-C_6)$-cycloalkyl-CO, $(C_5-C_6)$-cycloalkyl-$(C_1-C_2)$-alkyl-CO, optionally substituted $(C_1-C_8)$-aryl-CO, $(C_1-C_8)$-aryl-$(C_1-C_2)$-alkyl-CO optionally substituted in the aryl radical, $(C_1-C_6)$-alkyl-S$(O)_n$, $(C_5-C_6)$-cycloalkyl-S$(O)_n$, $(C_5-C_6)$-cycloalkyl-$(C_1-C_2)$-alkyl-S$(O)_n$, optionally substituted $(C_6-C_{12})$-aryl-S$(O)_n$, or $(C_1-C_8)$-aryl-$(C_1-C_2)$-alkyl-S$(O)_n$, optionally substituted in the aryl radical, where n is 1 or 2;

$R^1$ is $H_2N$—C(=NH), $H_2N$—C(=N—OH), $CH_3O$—CO—NH—C(=NH), $H_2N$—C(=NH)—NH or $H_2N$—$CH_2$;

$R^2$, $R^{2a}$ and $R^{2b}$ are hydrogen;

$R^3$ is $R^{11}NH$, $(C_{10}-C_{12})$-cycloalkyl, $(C_{10}-C_{12})$-cycloalkyl-$(C_1-C_3)$-alkyl, $(C_7-C_{12})$-bicycloalkyl, $(C_7-C_{12})$-bicycloalkyl-$(C_1-C_3)$-alkyl, $(C_{10}-C_{12})$-tricycloalkyl, $(C_{10}-C_{12})$-tricycloalkyl-$(C_1-C_3)$-alkyl, CO—$N(R^a)$—$R^4$—$E^a$ or CO—$R^5$—$R^6$—Het;

$R^{10}$ is hydroxyl, $(C_1-C_4)$-alkoxy, phenoxy, benzyloxy or $(C_1-C_4)$-alkylcarbonyloxy-$(C_1-C_4)$-alkoxy;

$R^{11}$ is $R^{15}O$—CO or $R^{15}S(O)_2$;

$R^{13}$ is $(C_1-C_6)$-alkyl, $(C_3-C_7)$-cycloalkyl or benzyl;

$R^{15}$ is $R^{16}$—$(C_1-C_3)$-alkyl or $R^{16}$;

$R^{16}$ is the radical of a 5-membered to 6-membered monocyclic ring or the radical of a 6-membered to 12-membered bicyclic or tricyclic ring, where these rings are saturated and can also contain one or two identical or different ring heteroatoms selected from the group of nitrogen and oxygen and can also be substituted by one, two or three identical or different $(C_1-C_4)$-alkyl radicals;

Het is the radical of a 5-membered to 6-membered monocyclic heterocycle bonded via a ring nitrogen atom, which is saturated and which can optionally contain one additional ring heteroatom selected from the group of oxygen and sulfur and which can be monosubstituted or disubstituted by identical or different substituents from the group consisting of $(C_1-C_4)$-alkyl, $(C_1-C_4)$-alkoxy, trifluoromethyl, phenyl and benzyl;

in all their stereoisomeric forms and mixtures thereof in all ratios, and their physiologically tolerable salts.

Particularly especially preferred compounds of the formula I are those in which, simultaneously W is $R^1$—A—$C(R^{13})$ and therein A is the divalent phenylene radical;

Y is a carbonyl group;

Z is $N(R^0)$;

B is a divalent methylene radical which is unsubstituted or substituted by a radical from the group consisting of $(C_1-C_6)$-alkyl, $(C_5-C_6)$-cycloalkyl, $(C_5-C_6)$-cycloalkyl-$(C_1-C_4)$-alkyl, phenyl, benzyl and phenylethyl;

E is $R^{10}CO$;

R, $R^a$ and $R^b$ independently of one another are hydrogen or $(C_1-C_4)$-alkyl;

$R^0$ is $(C_1-C_6)$-alkyl, $(C_6-C_{12})$-aryl-$(C_1-C_2)$-alkyl optionally substituted in the aryl radical, $(C_1-C_6)$-alkyl—S$(O)_2$ or $(C_6-C_{12})$-aryl-S$(O)_2$ optionally substituted in the aryl radical;

$R^1$ is $H_2N$—C(=NH), $H_2N$—C(=N—OH), $CH_3O$—CO—NH—C(=NH), $H_2N$—C(=NH)—NH or $H_2N$—$CH_2$;

$R^{2a}$, $R^{2b}$ and $R^{2b}$ are hydrogen;

$R^3$ is $R^{11}NH$ or CO—$R^5$—Het;

$R^5$ is the divalent radical of a natural or unnatural α-amino acid having a lipophilic side chain, where free functional groups can be protected by protective groups customary in peptide chemistry or can be present as esters or amides, and where the nitrogen atom of the N-terminal amino group carries a radical $R^b$;

$R^{10}$ is hydroxyl, $(C_1-C_4)$-alkoxy, phenoxy, benzyloxy or $(C_1-C_4)$-alkylcarbonyloxy-$(C_1-C_4)$-alkoxy;

$R^{11}$ is $R^{15}O$—CO or $R^{15}S(O)_2$;

$R^{13}$ is $(C_1-C_6)$-alkyl;

$R^{15}$ is $R^{16}$—$(C_1-C_3)$-alkyl or $R^{16}$;

$R^{16}$ is the radical of a 5-membered to 6-membered monocyclic ring or the radical of a 7-membered to 12-membered bicyclic or tricyclic ring, where these rings are saturated and can also contain one or two identical or different ring heteroatoms selected from the group of oxygen and nitrogen and can also be substituted by one or two identical or different $(C_1-C_4)$-alkyl radicals;

Het is the radical of a 5-membered or 6-membered monocyclic heterocycle bonded via a ring nitrogen atom, which is saturated and which can optionally contain one additional ring heteroatom selected from the group of oxygen and sulfur and which can be substituted by one or two identical or different $(C_1-C_4)$-alkyl radicals;

in all their stereoisomeric forms and mixtures thereof in all ratios, and their physiologically tolerable salts.

Very particularly especially preferred compounds of the formula I are those in which, simultaneously W is $R^1$—A—$C(R^{13})$ and therein A is the divalent phenylene radical;

Y is a carbonyl group;

Z is $N(R^0)$;

B is a divalent methylene radical which is unsubstituted or substituted by a radical from the group consisting of $(C_1-C_6)$-alkyl, $(C_5-C_6)$-cycloalkyl-$(C_1-C_4)$-alkyl, phenyl, benzyl and phenylethyl;

E is $R^{10}CO$;

R, $R^a$ and $R^b$ independently of one another are hydrogen or methyl;

$R^0$ is $(C_1-C_6)$-alkyl or $(C_1-C_8)$-aryl-$(C_1-C_2)$-alkyl optionally substituted in the aryl radical;

$R^1$ is $H_2N$—C(=NH), $H_2N$—C(=NOH), $CH_3O$—CO—NH—C(=NH), $H_2NH$—C(=NH)—NH or $H_2NH$—$CH_2$;

$R^2$, $R^{2a}$ and $R^{2b}$ are hydrogen;

$R^3$ is $R^{11}NH$ or CO—$R^5$—Het;

$R^5$ is the divalent radical of a natural or unnatural α-amino acid having a lipophilic side chain, where free functional groups can be protected by protective groups customary in peptide chemistry or can be present as esters or amides, and where the nitrogen atom of the N-terminal amino group carries a radical $R^b$;

$R^{10}$ is hydroxyl, $(C_1-C_4)$-alkoxy, phenoxy, benzyloxy or $(C_1-C_4)$-alkylcarbonyloxy-$(C_1-C_4)$-alkoxy;

$R^{11}$ is $R^{15}O$—CO;

$R^{13}$ is $(C_1-C_6)$-alkyl;

$R^{15}$ is $R^{16}$ or $R^{16}$—$CH_2$;

$R^{16}$ is cyclopentyl, cyclohexyl, 1-adamantyl, 2-adamantyl or noradamantyl;

Het is the radical of a 5-membered or 6-membered monocyclic heterocycle bonded via a ring nitrogen atom, which is saturated and which can optionally contain an oxygen atom as an additional ring heteroatom and which can be substituted by one or two identical or different $(C_1-C_4)$-alkyl radicals;

in all their stereoisomeric forms and mixtures thereof in all ratios, and their physiologically tolerable salts.

Generally, compounds of the formula I are preferred which have a uniform configuration at chiral centers, for example on the chiral carbon atom carrying the radicals $R^2$ and $R^3$ and/or on the center W in the 5-membered ring heterocycle in the formula I.

The compounds of the formula I can be prepared as desired, for example, by fragment condensation of a compound of the formula II

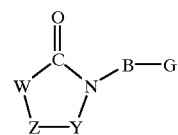

(II)

with a compound of the formula III,

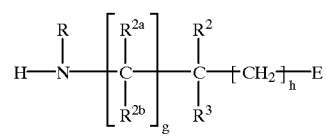

(III)

where, in the formulae II and III, the groups W, Y, Z, B, E, R, $R^2$, $R^{2a}$, $R^{2b}$ and $R^3$ as well as g and h are defined as indicated above or alternatively functional groups can be contained in protected form or in the form of precursors, and where G is hydroxycarbonyl, $(C_1-C_6)$-alkoxycarbonyl or activated carboxylic acid derivatives such as acid chlorides or active esters. If compounds of the formula I are to be prepared in which $R^3$ in the formula I is CO—$N(R^a)$—$R^4$—$E^a$ or CO—$R^5$—$R^6$—$R^7$ it is also possible, for example, that in the compounds of the formula III the radical $R^3$ initially is a hydroxycarbonyl group present in protected form, and that the desired group $R^3$ is built up then in one or more further condensation steps only after the condensation of the compounds of the formulae II and III.

For the condensation of the compounds of the formula II with those of the formula III, coupling methods of peptide chemistry well known to the person skilled in the art are advantageously used (see, for example, Houben-Weyl, Methoden der Organischen Chemie [Methods of Organic Chemistry], Volume 15/1 and 15/2, Georg Thieme Verlag, Stuttgart, 1974). Possible condensing agents are, for example, carbonyldiimidazole, carbodiimides such as dicyclohexylcarbodiimide or diisopropylcarbodiimide, O-((cyano(ethoxycarbonyl)methylene)amino)-N,N,N',N'-tetramethyluronium tetrafluoroborate (TOTU) or propylphosphonic anhydride (PPA). As a rule, it is necessary in the condensation to protect the nonreacting amino groups present by reversible protective groups. The same applies to carboxyl groups not involved in the reaction, which are preferably present during the condensation as $(C_1-C_6)$-alkyl esters, for example tert-butyl esters, or as benzyl esters. Amino group protection is unnecessary if the amino groups are still present in the form of precursors, for example as nitro groups or cyano groups, and are only formed after coupling, for example by hydrogenation. After coupling, the protective groups present are removed in a suitable manner. For example, $NO_2$ groups (guanidino protection), benzyloxycarbonyl groups and benzyl esters can be removed by hydrogenation. The protective groups of the tert-butyl type are removed under acidic conditions, while the 9-fluorenylmethyloxycarbonyl radical is removed by secondary amines.

Compounds of the formula II in which W is $R^1$—A—C($R^{13}$), Y is a carbonyl group and Z is $NR^0$ can be prepared, for example, by first reacting compounds of the formula IV

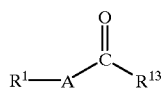

(IV)

in a Bucherer reaction to give compounds of the formula V

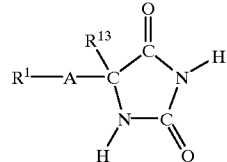

(V)

in which, as well as in the formula IV, $R^1$, $R^{13}$ and A are defined as indicated above (H. T. Bucherer, V. A. Lieb, J. Prakt. Chem. 141(1934), 5). Compounds of the formula VI

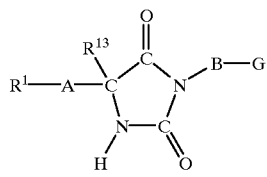

(VI)

in which $R^1$, $R^{13}$, A, B and G are defined as indicated above, can then be obtained by first reacting the compounds of the formula V, for example, with an alkylating reagent which introduces the radical —B—G into the molecule. The reaction of compounds of the formula VI with a second reagent of the formula $R^0$—LG, in which $R^0$ has the meanings indicated above and LG is a nucleophilically substitutable leaving group, for example halogen, in particular chlorine or bromine, ($C_1$–$C_4$)-alkoxy, optionally substituted phenoxy or a heterocyclic leaving group such as, for example, imidazolyl, leads to the corresponding compounds of the formula II. These reactions can be carried out analogously to known methods familiar to the person skilled in the art. Depending on the individual case, it may be appropriate here, as in all steps in the synthesis of the compounds of the formula I, to temporarily block functional groups which could lead to secondary reactions or undesired reactions by means of a protective group strategy tailored to the synthesis problem, as is known to the person skilled in the art. With respect to the preparation of the compounds of the formulae V and VI in racemic form and in enantiomerically pure form, reference is in particular made here to the corresponding embodiments described in WO-A-96/33976, which is incorporated herein by reference in its entirety.

If W is $R^1$—A—CH═C, this structural element can be introduced, for example, by condensing, analogously to known methods, an aldehyde with a 5-membered ring heterocycle which contains a methylene group in the position corresponding to the group W.

The amino compounds of the formula III can be synthesized, according to or analogously to standard procedures, from starting compounds which are commercially available or are obtainable according to or analogously to literature procedures.

Compounds of the formula I in which the 5-membered ring heterocycle is a dioxo- or thioxo-oxo-substituted imidazolidine ring in which W is $R^1$—A—C($R^{13}$) can also be obtained as follows:

By reaction of α-amino acids or N-substituted α-amino acids obtainable according to standard procedures or preferably their esters, for example the methyl ester, ethyl ester, tert-butyl ester or benzyl ester, for example of a compound of the formula VII

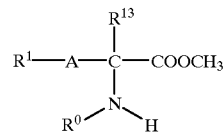

(VII)

in which $R^0$, $R^1$, $R^{13}$ and A are defined as indicated above, with an isocyanate or isothiocyanate, for example of the formula VIII

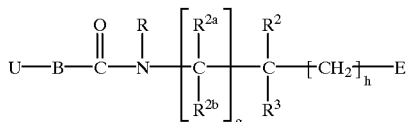

(VIII)

in which B, E, R, $R^2$, $R^{2a}$, $R^{2b}$, $R^3$, g and h are defined as indicated above and U is isocyanato or isothiocyanato, urea derivatives or thiourea derivatives, for example of the formula IX

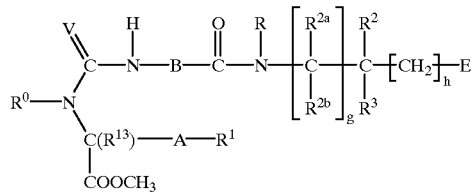

(IX)

are obtained for which the definitions indicated above apply and in which V is oxygen or sulfur, and which are cyclized by heating with acid with hydrolysis of the ester functions to give compounds of the formula Ia

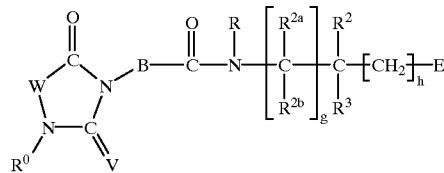

(Ia)

in which V is oxygen or sulfur, W is $R^1$—A—C($R^{13}$) and for which otherwise the meanings indicated above apply. The cyclization of the compounds of the formula IX to the compounds of the formula Ia can also be carried out by treatment with bases in inert solvents, for example by treatment with sodium hydride in an aprotic solvent such as dimethylformamide.

During the cyclization, guanidino groups can be blocked by protective groups, for example $NO_2$. Amino groups can be present in protected form or, for example, still as the $NO_2$ function or cyano function, which can later be reduced to the amino group or, in the case of the cyano group, also converted into the formamidino group.

Compounds of the formula I in which the 5-membered ring heterocycle is a dioxo- or thioxo-oxo-substituted imidazolidine ring in which W is $R^1$—A—$C(R^{13})$ can also be obtained by reacting a compound of the formula VII with an isocyanate or isothiocyanate of the formula X

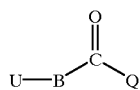
(X)

in which B and U are defined as indicated above for the formula VII and Q is an alkoxy group, for example a $(C_1-C_4)$-alkoxy group such as methoxy, ethoxy or tert-butoxy, a $(C_6-C_{14})$-aryloxy group, for example phenoxy, or a $(C_6-C_{14})$-aryl-$(C_1-C_4)$-alkoxy group, for example benzyloxy. In this case a compound of the formula XI

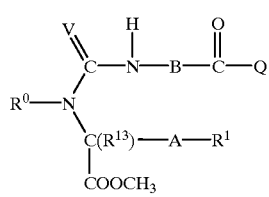
(XI)

is obtained in which V, A, B, Q, $R^0$, $R^1$ and $R^{13}$ are defined as indicated above for the formulae IX and X, which is then cyclized under the influence of an acid or of a base, such as described above for the cyclization of the compounds of the formula IX, to give a compound of the formula XII

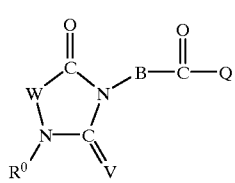
(XII)

in which W is $R^1$—A—$C(R^{13})$ and V, B, Q and $R^0$ are defined as indicated above for the formulae Ia and X. From the compound of the formula XII, a compound of the formula Ia is then obtained by hydrolysis of the group CO—Q to the carboxylic acid COOH and subsequent coupling with a compound of the formula III, as described above for the coupling of the compounds of the formulae II and III. Here too, during the cyclization functional groups can be present in protected form or present in the form of precursors.

A further method for the preparation of compounds of the formula Ia is, for example, the reaction of compounds of the formula XIII

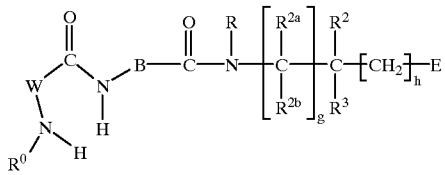
(XIII)

in which W is $R^1$—A—$C(R^{13})$ and for which otherwise the definitions indicated above apply, with phosgene, thiophosgene or corresponding equivalents (analogously to S. Goldschmidt and M. Wick, Liebigs Ann. Chem. 575 (1952), 211–231 and C. Tropp, Chem. Ber. 61 (1928), 1431–1439).

The conversion of an amino function into the guanidino function can be carried out using the following reagents:

1. O-Methylisourea (S. Weiss and H. Krommer, Chemiker Zeitung 98 (1974), 617–618)
2. S-Methylisothiourea (R. F. Borne, M. L. Forrester and I. W. Waters, J. Med. Chem. 20 (1977), 771–776)
3. Nitro-S-methylisothiourea (L. S. Hafner and R. E. Evans, J. Org. Chem. 24(1959)57)
4. Formamidinosulfonic acid (K. Kim, Y. -T. Lin and H. S. Mosher, Tetrah. Left. 29 (1988), 3183–3186)
5. 3,5-Dimethyl-1-pyrazolylformamidinium nitrate (F. L. Scott, D. G. O'Donovan and J. Reilly, J. Amer. Chem. Soc. 75 (1953), 4053–4054)
6. N,N'-Di-tert-butyloxycarbonyl-S-methylisothiourea (R. J. Bergeron and J. S. McManis, J. Org. Chem. 52 (1987),1700–1703)
7. N-Alkoxycarbonyl-, N,N'-dialkoxycarbonyl-, N-alkylcarbonyl- and N,N'-dialkylcarbonyl-S-methylisothiourea (H. Wollweber, H. Kolling, E. Niemers, A. Widdig, P. Andrews, H. -P. Schulz and H. Thomas, Arzneim. Forsch./Drug Res. 34 (1984), 531–542).

Amidines can be prepared from the corresponding cyano compounds by addition of alcohols (for example methanol or ethanol) in an acidic anhydrous medium (for example dioxane, methanol or ethanol) and subsequent aminolysis, for example treatment with ammonia in alcohols such as, for example, isopropanol, methanol or ethanol (G. Wagner, P. Richter and Ch. Garbe, Pharmazie 29 (1974), 12–55). A further method of preparing amidines is the addition of $H_2S$ to the cyano group, followed by a methylation of the resulting thioamide and subsequent reaction with ammonia (GDR Patent No. 235 866). Furthermore, hydroxylamine can be added to the cyano group, N-hydroxyamidines being formed which then if desired can also be converted into the amidines, for example by hydrogenation.

With respect to the preparation of the compounds of the formula I, reference is furthermore fully made to WO-A-96/33 976 and the following patents, in which compounds having platelet aggregation-inhibiting action are described: WO-A-94/21607, WO-A-95/14008, EP-A-449 079, EP-A-530 505 (U.S. Pat. No. 5,389,614), WO-A-93/18057, EP-A-566 919 (U.S. Pat. No. 5,397,796), EP-A-580 008 (U.S. Pat. No. 5,424,293) and EP-A-584 694 (U.S. Pat. No. 5,554, 594). All of these documents are incorporated by reference in their entirety.

The compounds of the formula I are valuable pharmaceutical active compounds which are suitable, for example, for the therapy and prophylaxis of inflammatory disorders, allergic disorders or asthma. The compounds of the formula I and their physiologically tolerable salts can be administered according to the invention to animals, preferably to mammals, and in particular to man, as pharmaceuticals for therapy or prophylaxis. They can be administered per se, in mixtures with one another or in the form of pharmaceutical preparations which permit enteral or parenteral administration and which as active constituent contain an efficacious dose of at least one compound of the formula I and/or its physiologically tolerable salts in addition to customary pharmaceutically innocuous excipients and/or additives.

The present invention therefore also relates to the compounds of the formula I and/or their physiologically tolerable salts for use as pharmaceuticals, the use of the compounds of the formula I and/or their physiologically tolerable salts for the production of pharmaceuticals for the therapy and prophylaxis of the diseases described above or in the following, for example for the therapy and prophylaxis of inflammatory disorders, and the use of the compounds of the formula I and/or their physiologically tolerable salts in the therapy and prophylaxis of these diseases. The present invention furthermore relates to pharmaceutical preparations which contain an efficacious dose of at least one compound of the formula I and/or its physiologically tolerable salts in addition to customary pharmaceutically innocuous excipients and/or additives.

The pharmaceuticals can be administered orally, for example in the form of pills, tablets, film-coated tablets, sugar-coated tablets, granules, hard and soft gelatin capsules, solutions, syrups, emulsions or suspensions. However, administration can also be carried out rectally, for example in the form of suppositories, or parenterally, for example in the form of injection or infusion solutions, microcapsules or rods, or percutaneously, for example in the form of ointments, solutions or tinctures, or in another way, for example in the form of nasal sprays or aerosol mixtures.

The pharmaceutical preparations according to the invention are prepared in a manner known per se, pharmaceutically inert inorganic or organic excipients being used in addition to the compound(s) of the formula I and/or its/their physiologically tolerable salts. For the preparation of pills, tablets, sugar-coated tablets and hard gelatin capsules, it is possible to use, for example, lactose, cornstarch or derivatives thereof, talc, stearic acid or its salts etc. Excipients for soft gelatin capsules and suppositories are, for example, fats, waxes, semisolid and liquid polyols, natural or hardened oils etc. Suitable excipients for the preparation of solutions, for example injection solutions, or of emulsions or syrups are, for example, water, alcohols, glycerol, polyols, sucrose, invert sugar, glucose, vegetable oils etc. Suitable excipients for microcapsules, implants or rods are, for example, copolymers of glycolic acid and lactic acid. The pharmaceutical preparations normally contain approximately 0.5 to 90% by weight of the compounds of the formula I and/or their physiologically tolerable salts.

In addition to the active compounds and excipients, the pharmaceutical preparations can additionally contain additives, such as, for example, fillers, disintegrants, binders, lubricants, wetting agents, stabilizers, emulsifiers, preservatives, sweeteners, colorants, flavorings or aromatizers, thickeners, diluents, buffer substances, and also solvents or solubilizers or means for achieving a depot effect, as well as salts for altering the osmotic pressure, coating agents or antioxidants. They can also contain two or more compounds of the formula I and/or their physiologically tolerable salts. Furthermore, they can also contain one or more other therapeutically or prophylactically active substances in addition to at least one compound of the formula I and/or its physiologically tolerable salts, for example substances having antiinflammatory action. The pharmaceutical preparations normally contain 0.2 to 500 mg, preferably 1 to 100 mg, of active compound of the formula I and/or its physiologically tolerable salts.

The compounds of the formula I have the ability to inhibit cell-cell and cell-matrix interaction processes in which interactions between VLA4 with its ligands play a part. The efficacy of the compounds of the formula I can be demonstrated, for example, in an assay in which the binding of cells which contain the VLA4 receptor, for example of leucocytes, to ligands of this receptor is measured, for example to VCAM-1, which for this purpose can advantageously also be prepared by genetic engineering. Details of such an assay are described below. In particular, the compounds of the formula I are able to inhibit the adhesion and the migration of leucocytes, for example the adhesion of leucocytes to endothelial cells which—as explained above—is controlled via the VCAM-1/VLA4 adhesion mechanism. Besides as antiinflammatory agents, the compounds of the formula I and their physiologically tolerable salts are therefore generally suitable for the therapy and prophylaxis of diseases which are based on the interaction between the VLA-4 receptor and its ligands or can be affected by an inhibition of this interaction, and in particular they are suitable for the therapy and prophylaxis of diseases which are caused at least partially by an undesired extent of leucocyte adhesion and/or leucocyte migration or are associated therewith, or for whose prevention, alleviation or cure the adhesion and/or migration of leucocytes should be decreased.

The compounds of the formula I can be employed as antiinflammatories in the case of inflammatory symptoms of very different cause. They are used, for example, for the therapy or prophylaxis of rheumatoid arthritis, of inflammatory bowel disease (ulcerative colitis), of systemic lupus erythematosus or for the therapy or prophylaxis of inflammatory disorders of the central nervous system such as, for example, multiple sclerosis, for the therapy or prophylaxis of asthma or of allergies, for example allergies of the delayed type (type IV allergy). They are furthermore suitable for the therapy or prophylaxis of cardiovascular disorders, arteriosclerosis, of restenoses, for the therapy or prophylaxis of diabetes, for the prevention of damage to organ transplants, for the inhibition of tumor growth or formation of tumor metastases in various malignancies, for the therapy of malaria as well as of other diseases in which blocking of the integrin VLA4 and/or influencing of the leucocyte activity appears appropriate for prevention, alleviation or cure.

The dose when using the compounds of the formula I can vary within wide limits and is to be tailored to the individual conditions in each individual case as is customary. It depends, for example, on the compound employed or on the nature and severity of the disease to be treated or on whether an acute or chronic disease state is treated or whether prophylaxis is conducted. In general, in the case of oral administration a daily dose of approximately 0.01 to 100 mg/kg, preferably 0.1 to 10 mg/kg, in particular 0.3 to 2 mg/kg (in each case per kg of body weight) is appropriate in an adult weighing about 75 kg to achieve effective results. In the case of intravenous administration, the daily dose is in general approximately 0.01 to 50 mg/kg, preferably 0.01 to 10 mg/kg of body weight. In particular when relatively large amounts are administered, the daily dose can be divided into a number, for example 2, 3 or 4, part administrations. If appropriate, depending on individual behavior, it may be necessary to deviate upward or downward from the indicated daily dose.

A subject of the present invention also are the compounds of the formula I for the inhibition of the adhesion and/or migration of leucocytes or for the inhibition of the VLA-4 receptor and the use of the compounds of the formula I for the production of pharmaceuticals therefor, i.e., of pharmaceuticals for the therapy or prophylaxis of diseases in which leucocyte adhesion and/or leucocyte migration exhibits an undesired extent, or of diseases in which VLA4-dependent adhesion processes play a part, as well as the use of the compounds of the formula I and/or their physiologically tolerable salts in the therapy and prophylaxis of diseases of this type.

The compounds of the formula I and their salts can furthermore be employed for diagnostic purposes, for example in in-vitro diagnoses, and as auxiliaries in biochemical investigations in which VLA4 blocking or influencing of cell-cell or cell-matrix interactions is intended. They can furthermore be used as intermediates for the preparation of other compounds, in particular of other pharmaceutical active compounds which are obtainable from the compounds of the formula I, for example, by modification or introduction of radicals or functional groups.

The invention is further described with reference to the following examples. The examples are for illustration purposes only and do not limit the scope of the invention.

EXAMPLES

The compounds were identified by means of mass spectra (MS) and/or NMR spectra. Compounds which were purified by chromatography using an eluent which contained, for example, acetic acid or trifluoroacetic acid, and then freeze-dried, sometimes still contained the acid derived from the eluent, depending on how the freeze drying was carried out, and were thus obtained partially or completely in the form of a salt of the acid used, for example in the form of the acetic acid salt or trifluoroacetic acid salt.

The abbreviations have the following meanings:

| | |
|---|---|
| DMF | N,N-dimethylformamide |
| THF | tetrahydrofuran |
| DCC | N,N'-dicyclohexylcarbodiimide |
| HOBt | 1-hydroxybenzotriazole |
| HOOBt | 3-hydroxy-4-oxo-3,4-dihydro-1,2,3-benzotriazine |

Example 1

(S)-3-(((R,S)-4-(4-(Amino-imino-methyl)phenyl)-3-benzyl-4-methyl-2,5-dioxoimidazolidin-1-yl)acetylamino)-2-(1-adamantylmethyloxy-carbonylamino)propionic acid

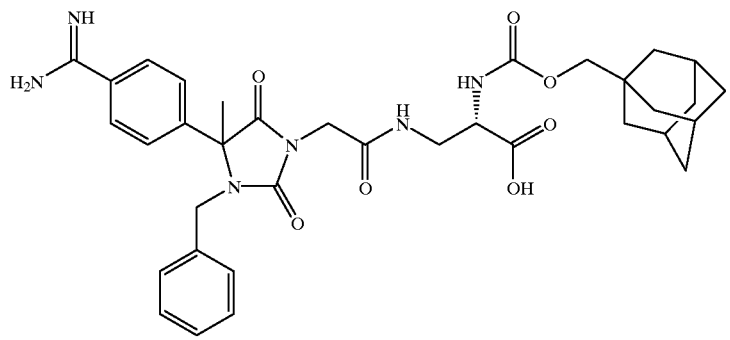

1a) (R,S)-4-(4-Cyanophenyl)-4-methyl-2,5-dioxoimidazolidine 20 g (138 mmol) of p-acetylbenzonitrile, 115.6 g of ammonium carbonate (1.21 mol) and 11.6 g of potassium cyanide (178 mmol) were dissolved in 600 ml of a mixture of 50% ethanol and 50% water. The mixture was stirred at 55° C. for 5 hours and allowed to stand overnight at room temperature. The solution was adjusted to a pH of 6.3 using 6 N hydrochloric acid and then stirred at room temperature for two hours. The precipitate was filtered off with suction, washed with water and dried over phosphorus pentoxide in a high vacuum. Yield: 22.33 g (75%).

1b) Methyl ((R,S)-4-(4-cyanophenyl)4-methyl-2,5-dioxoimidazolidin-1-yl)acetate 1.068 g of sodium (46.47 mmol) were dissolved in 110 ml of absolute methanol under nitrogen. The clear solution was treated with 10 g of (R,S)-4-(4-cyanophenyl)-4-methyl-2,5-dioxoimidazoline (46.47 mmol) and the mixture was refluxed for 2 h. 7.75 g (46.68 mmol) of potassium iodide were added and a solution of 4.53 ml of methyl chloroacetate (51.3 mmol) in 5 ml of methanol was added dropwise in the course of one hour. The mixture was heated to boiling for 6 hours, allowed to stand overnight at room temperature and concentrated. The oily residue was chromatographed on silica gel using methylene chloride/ethyl acetate (9:1).

Yield: 8.81 g (66%).

1c) Methyl ((R,S)-4-(4-cyanophenyl)-3-benzyl-4-methyl-2,5-dioxoimidazolidin-1-yl)acetate 754 mg (17.27 mmol) of sodium hydride were added to a solution of 4.5 g (15.7 mmol) of methyl ((R,S)-4-(4- cyanophenyl)-4-methyl-2,5-dioxo-imidazolidin-1-yl) acetate in 25 ml of absolute DMF under argon at 0° C., the mixture was stirred at room temperature for 15 min, 2.05 ml (17.27 mmol) of benzyl bromide were added and the mixture was stirred at room temperature for 4 h. The solvent was removed in vacuo and the residue was chromatographed on silica gel using heptane/ethyl acetate (7:3). After concentration of the product fractions, 9.81 g (76%) of the title compound were obtained.

1d) Methyl ((R,S)-4-(4-amino-imino-methyl)phenyl)-3-benzyl-4-methyl-2,5-dioxoimidazolidin-1-yl)acetate hydrochloride A suspension of 4.42 g (11.7 mmol) of methyl ((R,S)4-(4-cyanophenyl)-3-benzyl-4-methyl-2,5-dioxoimidazolidin-1-yl)acetate in 80 ml of absolute ethanol was cooled to 0° C. Dry hydrogen chloride gas was passed into the suspension, the temperature always being kept below 10° C., until the nitrile band was no longer present in the IR spectrum. The ethanolic solution was concentrated to one half and treated with 1 l of diethyl ether. The suspension was concentrated in vacuo and the residue was dried in a high vacuum. The intermediate thus obtained was dissolved in 60 ml of absolute isopropanol and treated at 50° C. with 13.7 ml of a 1.9 N solution of ammonia in isopropanol. After stirring at 50° C. for 5 h, the reaction mixture was cooled and poured into 1 l of diethyl ether. The precipitate was filtered off with suction, the filtrate was concentrated, and both residues were combined and purified by chromatography on silica gel using dichloromethane/methanol/acetic acid/water (9:1:0.1:0.1). 2.94 g (64%) of the title compound were obtained.

1e) ((R,S)-4-(4-Amino-imino-methyl)phenyl)-3-benzyl-4-methyl-2,5-dioxoimidazolidin-1-yl)acetic acid hydrochloride 2.82 g (7.2 mmol) of methyl ((R,S)-4-(4-amino-imino-methyl)phenyl)-3-benzyl-4-methyl-2,5-dioxoimidazolidin-1-yl)acetate hydrochloride were heated under reflux for 5 h in 60 ml of conc. hydrochloric acid. The solution was concentrated in vacuo, and the residue was diluted with water and freeze-dried. 1.885 g (63%) of the title compound were obtained.

1f) tert-Butyl (S)-3-amino-2-benzyloxycarbonylaminopropionate 10 g (42 mmol) of (S)-3-amino-2-benzyloxycarbonylaminopropionic acid were shaken in a mixture of 100 ml of dioxane, 100 ml of isobutylene and 8 ml of conc. $H_2SO_4$ in an autoclave under an $N_2$ pressure of 20 atm for 3 days. Excess isobutylene was blown out and 150 ml of diethyl ether and 150 ml of saturated $NaHCO_3$ solution were added to the remaining solution. The phases were separated and the aqueous phase was extracted 2x with 100 ml of diethyl ether each time. The combined organic phases were washed 2x with 100 ml of water each time and dried over $Na_2SO_4$. After removing the solvent in vacuo, 9.58 g (78%) of the title compound were obtained as a pale yellow oil.

1g) tert-Butyl (S)-2-benzyloxycarbonylamino-3-tert-butoxycarbonylamino-propionate 8.9 g (40.8 mmol) of di-tert-butyl dicarbonate and then, in portions, 1 N NaOH were added to a solution of 10 g (34 mmol) of tert-butyl (S)-3-amino-2-benzyloxycarbonylaminopropionate in 600 ml of THF/water (2:1) at 0° C. such that the pH of the solution was between 9 and 10 (consumption of 1 N NaOH:32 ml). After stirring at room temperature for 3 h, 1 l of water was added and the mixture was extracted 3 times with diethyl ether. After drying over sodium sulfate, filtration and removal of the solvent in vacuo, the residue was chromatographed on silica gel using dichloromethane/methanol (20:1). 13.19 g (98%) of the title compound were obtained.

1h) tert-Butyl (S)-2-amino-3-tert-butoxycarbonylaminopropionate hydrochloride 13.1 g of tert-butyl (S)-2-benzyloxycarbonylamino-3-tert-butoxycarbonylaminopropionate were hydrogenated over 10% Pd/C in methanol/HCl. After 1.5 h, the mixture was filtered and the filtrate was concentrated in vacuo. 9.77 g (99%) of the title compound were obtained as a colorless solid.

1i) tert-Butyl (S)-2-(1-adamantylmethyloxycarbonylamino)-3-tert-butoxycarbonylaminopropionate A solution of 10.9 g (65.4 mmol) of 1-(hydroxymethyl) adamantane and 10.6 g (65.4 mmol) of carbonyldiimidazole in 60 ml of THF was stirred at 50° C. for 1.5 h. 9.7 g (32.7 mmol) of tert-butyl (S)-2-amino-3-tert-butoxycarbonylaminopropionate hydrochloride in 25 ml of THF and 5.6 ml (32.7 mmol) of diisopropylethylamine were added, and the mixture was stirred for 4 h at 60° C. and allowed to stand at room temperature overnight. The solvent was removed in vacuo and the residue was chromatographed on silica gel using heptanelethyl acetate (7:3). 8.7 g (59%) of the title compound were obtained as a colorless oil.

1j) tert-Butyl (S)-2-(1-adamantylmethyloxycarbonylamino)-3-amino-propionate

A solution of 8.7 g (19.22 mmol) of tert-butyl (S)-2-(1-adamantylmethyloxy-carbonylamino)-3-tert-butoxycarbonylamino-propionate in 180 ml of trifluoroacetic acid/dichloromethane (1:1) was added after 1 min to 1.5 l of ice-cold $NaHCO_3$ solution, the mixture was extracted three times with dichloromethane and the combined dichloromethane phases were then dried over sodium sulfate. After filtration and removal of the solvent in vacuo, 6.35 g (94%) of the title compound were obtained as a colorless solid.

1k) (S)-3-(((R,S)-4-(4-(Amino-imino-methyl)phenyl)-3-benzyl-4-methyl-2,5-dioxoimidazolidin-1-yl)acetylamino)-2-(1-adamantylmethyloxy-carbonylamino)propionic acid 417 mg (1 mmol) of ((R,S)-4-(4-(amino-imino-methyl) phenyl)-3-benzyl-4-methyl-2,5-dioxoimidazolidin-1-yl) acetic acid hydrochloride and 163 mg (1 mmol) of HOOBt were suspended in 5 ml of DMF and treated at 0° C. with 220 mg (1.1 mmol) of DCC. The mixture was stirred for 1 h at 0° C. and for 1 h at room temperature and 353 mg (1 mmol) of tert-butyl (S)-2-(1-adamantylmethyloxycarbonylamino)-3-aminopropionate and 11.7 μl (0.9 mmol) of N-ethylmorpholine were then added, and the mixture was stirred for 2 h at room temperature and allowed to stand at room temperature overnight. After filtration, the filtrate was concentrated in vacuo and the residue was chromatographed on silica gel using dichloromethane/methanol/glacial acetic acid/water (9:1:0.1:0.1). After concentration of the product fractions, the residue was dissolved in 4 ml of 90% strength trifluoroacetic acid and stirred at room temperature for 1 h. The trifluoroacetic acid was removed in vacuo, the residue was partitioned between diethyl ether and water, the water phase was concentrated and the residue was purified by chromatography on silica gel using dichloromethane/methanol/ glacial acetic acid/water (9:1:0.1:0.1) and subsequent preparative HPLC on RP-18. After concentrating the product fractions and freeze-drying, 26.3 mg (4%) of the title compound were obtained.

FAB-MS: 659.4 $(M+H)^+$

Example 2

(S)-3-((S)-4-(4-(Amino-hydroximino-methyl)phenyl)-3-(2-naphthylmethyl)-4-methyl-2,5-dioxoimidazolidin-1-yl)

acetylamino)-2-(1-adamantylmethyloxy-carbonylamino) propionic acid 2d) tert-Butyl (S)-3-((S)-4-(4-(amino-hydroximino-methyl)phenyl)-3-(2-naphthylmethyl)-4-methyl-2,5-

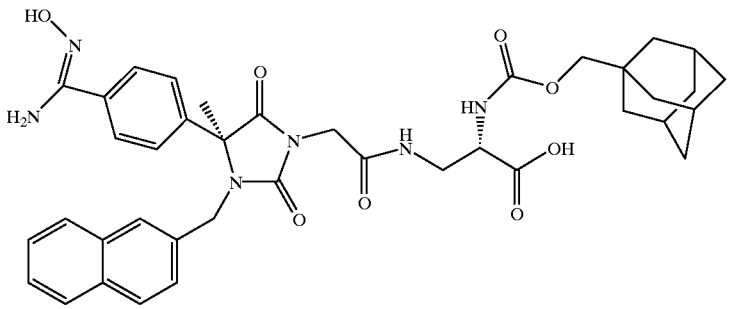

dioxoimidazolidin-1-yl)acetylamino)-2-(1-adamantylmethyloxycarbonylamino)propionate 164 mg (0.5 mmol) of TOTU (O-(cyano(ethoxycarbonyl) methylenamino)-1,1,3,3-tetramethyluronium tetrafluoroborate) and 165 mg (1.26 mmol) of diisopropyl-ethylamine were added to a solution of 223 mg (0.5 mmol) of ((S)-4-(4-(amino-hydroximino-methyl)phenyl)-3-(2-naphthylmethyl)-4-methyl-2,5-dioxoimidazolidin-1-yl) acetic acid and 176 mg (0.5 mmol) of tert-butyl (S)-2-(1-adamantylmethyloxycarbonylamino)-3-aminopropionate (see Example 1) in 10 ml of absolute DMF. After stirring at room temperature for 2 h and standing overnight, the reaction mixture was concentrated in vacuo and the residue was partitioned between ethyl acetate and water. The phases were separated, the water phase was extracted with ethyl acetate and the combined organic phases were washed with saturated NaHCO₃ solution and water. After drying over sodium sulfate, filtration and concentration of the filtrate in vacuo, the residue was taken up in ethyl acetate and the solution was washed successively with KHSO₄/K₂SO₄ solution, saturated NaHCO₃ solution and water and dried over magnesium sulfate. 240 mg (62%) of the title compound were obtained.

2e) (S)-3-((S)-4-(4-(Amino-hydroximino-methyl) phenyl)-3-(2-naphthyl-methyl)-4-methyl-2,5-dioxoimidazolidin-1-yl)acetylamino)-2-(1-adamantylmethyloxycarbonylamino)propionic acid 220 mg (0.28 mmol) of tert-butyl (S)-3-((S)-4-(4-(amino-hydroximino-methyl)phenyl)-3-(2-naphthylmethyl)-4-methyl-2,5-dioxoimidazolidin-1-yl)acetylamino)-2-(1-adamantylmethyloxycarbonylamino)propionate were dissolved in 20 ml of 90% strength trifluoroacetic acid. After 1 h at room temperature, the trifluoroacetic acid was removed in vacuo and the residue was stirred with diethyl ether. The product was filtered off with suction, washed with diethyl ether and dried in a high vacuum. 110 mg (54%) of the title compound were obtained (as the trifluoroacetic acid salt).

ES(+)—MS: 725.4 (M+H)⁺

2a) 2-Naphthylmethyl ((S)-4-(4-cyanophenyl)-3-(2-naphthylmethyl)-4-methyl-2,5-dioxoimidazolidin-1-yl) acetate 5.28 g (110 mmol) of sodium hydride were added to a solution of 13.66 g (50 mmol) of ((S)-4-(4-cyanophenyl)-4-methyl-2,5-dioxoimidazolidin-1-yl)acetic acid in 100 ml of absolute DMF with ice-cooling. After stirring at room temperature for 1 h, 24.3 g (110 mmol) of 2-bromomethyl-naphthalene were added in the course of 1 h. The reaction mixture was stirred at room temperature for 20 h and then poured into a mixture of ethyl acetate/water. After phase separation, the water phase was extracted with ethyl acetate. The combined organic phases were washed twice with water and dried over magnesium sulfate. After filtration and removal of the solvent in vacuo, the residue was chromatographed on silica gel using heptane/ethyl acetate (2:1). 8.51 g (56%) of the title compound were obtained.

2b) 2-Naphthylmethyl ((S)-4-(4-(amino-hydroximino-methyl)phenyl)-3-(2-naphthylmethyl)-4-methyl-2,5-dioxoimidazolidin-1-yl)acetate 1.67 g (24 mmol) of hydroxylammonium chloride and 5.04 ml (36 mmol) of triethylamine were added to a solution of 6.64 g (12 mmol) of 2-naphthylmethyl ((S)-4-(4-cyanophenyl)-3-(2-naphthylmethyl)-4-methyl-2,5-dioxoimidazolidin-1-yl)acetate in 120 ml of absolute ethanol and the mixture was heated under reflux for 2.5 h. The solvent was removed in vacuo and the residue was partitioned between ethyl acetate and water. The phases were separated and the water phase was extracted with ethyl acetate. The combined organic phases were washed with water and dried over magnesium sulfate. After filtration, the solvent was removed in vacuo and 6.08 g (86%) of the title compound were obtained.

2c) ((S)-4-(4-(Amino-hydroximino-methyl)phenyl)-3-(2-naphthylmethyl)-4-methyl-2,5-dioxoimidazolidin-1-yl) acetic acid 2 g (3.4 mmol) of 2-naphthylmethyl ((S)-4-(4-(amino-hydroximino-methyl)phenyl)-3-(2-naphthylmethyl)-4-methyl-2,5-dioxoimidazolidin-1-yl)acetate in 200 ml of absolute methanol were hydrogenated over palladium hydroxide/barium sulfate for 4 h. The catalyst was filtered off, the filtrate was concentrated in vacuo and the residue was stirred with ethyl acetate. The product was filtered off with suction and dried in a high vacuum. 0.56 g (37%) of the title compound was obtained.

Example 3

(S)-3-(((R,S)-4-(4-(Amino-imino-methyl)phenyl)-3-benzyl-4-methyl-2,5-dioxoimidazolidin-1-yl)acetylamino)-2-benzylaminocarbonylaminopropionic acid

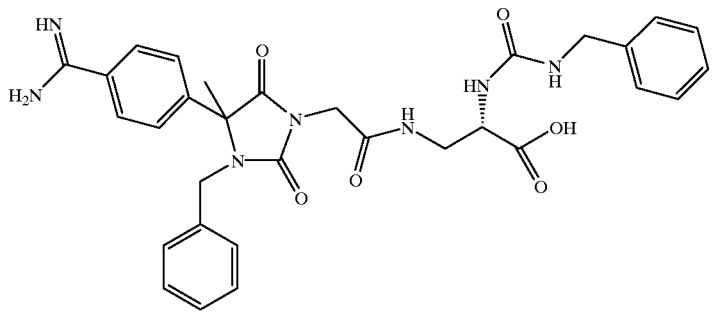

3a) (S)-3-(((R,S)-4-(4-(Amino-imino-methyl)phenyl)-3-benzyl-4-methyl-2,5-dioxoimidazolidin-1-yl)acetylamino)-2-aminopropionic acid dihydrochloride A solution of 4.4 g (6.7 mmol) of (S)-3-(((R,S)-4-(4-(amino-imino-methyl)-phenyl)-3-benzyl-4-methyl-2,5-dioxoimidazolidin-1-yl)acetylamino)-2-benzyloxycarbonylaminopropionic acid (prepared by coupling of ((R,S)-4-(4-amino-imino-methyl)phenyl)-3-benzyl-4-methyl-2,5-dioxoimidazolidin-1-yl)acetic acid hydrochloride and tert-butyl (S)-3-amino-2-benzyloxy-carbonylaminopropionate analogously to Example 1 and subsequent cleavage of the tert-butyl ester analogously to Example 1) in 100 ml of methanol was hydrogenated at room temperature for 1 h over palladium hydroxide/barium sulfate. The catalyst was filtered off, the solvent was removed in vacuo and the residue was stirred at 40° C. for 30 min in 40 ml of 6 N hydrochloric acid. The solution was concentrated in vacuo, diluted with water and freeze-dried. 2.39 g (77%) of the title compound were obtained.

product was purified by chromatography on silica gel using dichloromethane, dichloromethane/methanol (8:2) and finally methanol. After concentration of the product fractions, the residue was dissolved in water and freeze-dried. 70 mg (10%) of the title compound were obtained.

FAB—MS: 600.3 (M+H)⁺

Example 4

(S)-(((R,S)-4-(4-(Amino-imino-methyl)phenyl)-3-benzyl-4-methyl-2,5-dioxoimidazolidin-1-yl)acetylamino)-2-benzylaminothiocarbonylamino-propionic acid

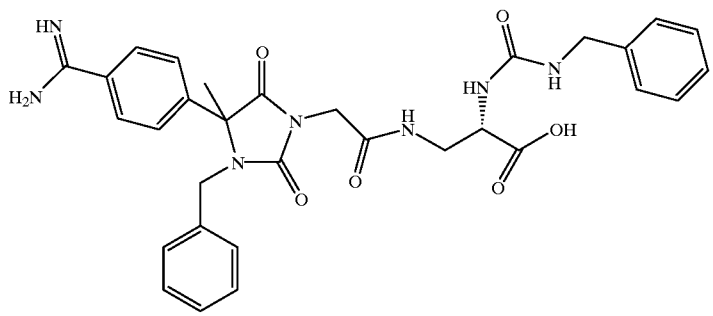

3b) (S)-3-(((R,S)-4-(4-(Amino-imino-methyl)phenyl)-3-benzyl-4-methyl-2,5-dioxoimidazolidin-1-yl)acetylamino)-2-benzylaminocarbonylaminopropionic acid 0.4 ml of diisopropylethylamine (2.4 mmol) and 0.15 ml (1.2 mmol) of benzyl isocyanate were added to a solution of 570 mg (1.2 mmol) of (S)-3-(((R,S)-4-(4-(amino-imino-methyl)phenyl)-3-benzyl-4-methyl-2,5-dioxo-imidazolidin-1-yl)acetylamino)-2-aminopropionic acid dihydrochloride in 20 ml of absolute DMF. After stirring at room temperature for 4 h, the solvent was removed in vacuo and the crude The compound was obtained analogously to Example 3 by employing benzyl isothiocyanate instead of benzyl isocyanate.

ES(+)—MS: 616.3 (M+H)⁺

Example 5

((R,S)-4-(4-(Amino-imino-methyl)phenyl)-3-(2-naphthylmethyl)-4-methyl-2,5-dioxoimidazolidin-1-yl)acetyl-L-(N-methylaspartyl)-L-valine morpholide

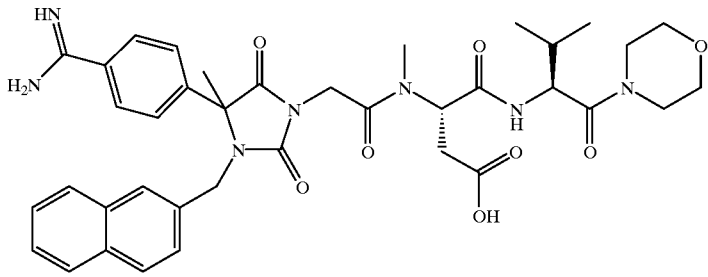

5a) L-Valine morpholide 3.93 g (12 mmol) of TOTU (see Example 2) and 2.04 ml of diisopropyl-ethylamine were added to a solution of 3.01 g (12 mmol) of N-benzyloxy-carbonyl-L-valine and 1.04 g (12 mmol) of morpholine in 30 ml of absolute DMF. After stirring at room temperature for 2 h, the solvent was removed in vacuo, the residue was taken up in ethyl acetate and the solution was successively washed 3× with an aqueous $KHSO_4/K_2SO_4$ solution, 3× with a saturated $NaHCO_3$ solution and 3× with water. After drying over sodium sulfate, filtration and removal of the solvent in vacuo, 3.88 g of N-benzyloxycarbonyl-L-valine morpholide were obtained as a crude product which was hydrogenated in methanol for 3 h over 10% Pd/C to remove the benzyloxycarbonyl group. 2.11 g (95%) of the title compound were obtained.

5b) L-(N-Methylaspartyl(OtBu))-L-valine morpholide

The compound was prepared by coupling of L—Z—N($CH_3$)—Asp(OtBu)—OH with L-valine morpholide and subsequent hydrogenolytic cleavage of the Z group (benzyloxycarbonyl group) as described under a). From 1.39 g (7.5 mmol) of L-valine morpholide, 2.4 g (86%) of the title compound were thus obtained.

5c) ((R,S)-4-(4-(Amino-imino-methyl)phenyl)-3-(2-naphthylmethyl)-4-methyl-2,5-dioxoimidazolidin-1-yl) acetyl-L-(N-methylaspartyl)-L-valine morpholide The compound was obtained by coupling of ((R,S)-4-(4-(amino-imino-methyl)phenyl)-3-(2-naphthylmethyl)-4-methyl-2,5-dioxoimidazolidin-1-yl)acetic acid hydrochloride (prepared analogously to Example 1 using 2-bromomethylnaphthalene instead of benzyl bromide) and L-(N-methyl-aspartyl(OtBu))-L-valine morpholide and subsequent cleavage of the tert-butyl ester with 90% strength trifluoroacetic acid analogously to Example 2.

ES(+)—MS: 728.4 (M+H)$^+$

Further carbamates can be obtained analogously to the compound of Example 1, for example (S)-3-(((S)-4-(4-(amino-imino-methyl)phenyl)-3-benzyl-4-methyl-2,5-dioxoimidazolidin-1-yl)-((R,S)-2-(2-methylpropyl) acetylamino)-2-(cyclohexylmethyloxycarbonylamino) propionic acid of the formula

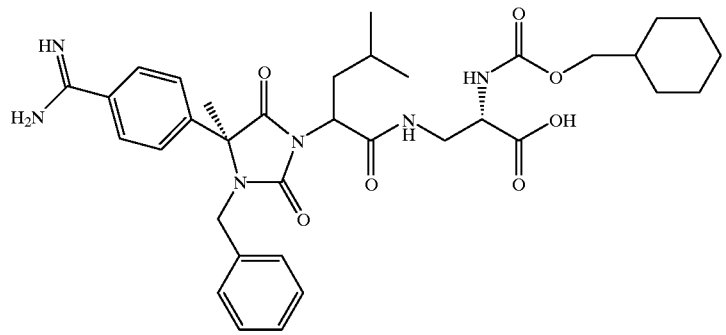

where instead of the chloroacetic acid ester employed in Example 1 in step b), for example, a 2-bromo-4-methylpentanoic acid ester can be employed.

Investigation of the biological activity

The test method used for the activity of the compounds of the formula I on the interaction between VCAM-1 and VLA-4 is an assay which is specific for this interaction. The cellular binding components, i.e., the VLA4 integrins, are supplied in their natural form as surface molecules on human U937 cells (ATCC CRL 1593), which belong to the leucocytes group. The specific binding components used are genetically engineered recombinant soluble fusion proteins, consisting of the extracytoplasmatic domain of human VCAM-1 and the constant region of a human immunoglobulin of the subclass IgG1.

Test method

Assay for the measurement of the adhesion of U937 cells (ATCC CRL 1593) to hVCAM-1 (1–3)-IgG 1. Preparation of human VCAM-1(1–3)-IgG and human CD4-IgG A genetic construct for the expression of the extracellular domain of human VCAM-1, associated with the genetic sequence of the heavy chain of human immunoglobulin IgG1 (hinge, CH2 and CH3 regions), from Dr. Brian Seed, Massachusetts General Hospital, Boston, USA (cf. Damle and Aruffo, Proc. Natl. Acad. Sci. USA 1991, 88, 6403–6407) was employed. The soluble fusion protein hVCAM-1 (1–3)-IgG contained the three amino-terminal extracellular immunoglobulin-like domains of human VCAM-1 (Damle and Aruffo, Proc. Natl. Acad. Sci. USA 1991, 88, 6403). CD4-IgG (Zeftimeissl et al., DNA and Cell Biology 1990, 9, 347) served as a fusion protein for negative controls. The recombinant proteins were expressed as soluble proteins after DEAE/dextran-mediated DNA transfection in COS cells (ATCC CRL1651) according to standard procedures (Ausubel et al., Current Protocols in Molecular Biology, John Wiley & Sons, Inc., 1994).

2. Assay for the measurement of the adhesion of U937 cells to hVCAM-1 (1–3)-IgG 2.1 96-well microtiter test plates (Nunc Maxisorb) were incubated at room temperature for 1 hour with 100 μl/well of a goat-anti-human-IgG antibody solution (10 μg/ml in 50 mM tris, pH 9.5). After removal of the antibody solution, washing was carried out once with PBS.

2.2 150 μl/well of a blocking buffer (1% BSA in PBS) was incubated on the plates at room temperature for 0.5 hour. After removal of the blocking buffer, washing was carried out once with PBS.

2.3 100 μl per well of a cell culture supernatant of transfected COS cells was incubated on the plates at room temperature for 1.5 hours. The COS cells were transfected with a plasmid which codes for the three N-terminal immunoglobulin-like domains of VCAM-1, coupled to the Fc part of human IgG$_1$ (hVCAM-1(1—3)-IgG). The content of hVCAM-1 (1–3)-IgG was about 0.5–1 μg/ml. After removal of the culture supernatant washing was carried out once with PBS.

2.4 The plates were incubated at room temperature for 20 minutes with 100 μl/well of Fc receptor blocking buffer (1 mg/ml of γ-globulin, 100 mM NaCl, 100 μM MgCl$_2$, 100 μM MnCl$_2$, 100 μM CaCl$_2$, 1 mg/ml of BSA in 50 mM HEPES, pH 7.5). After removal of the Fc receptor blocking buffer washing was carried out once with PBS.

2.5 20 μl of binding buffer (100 mM NaCl, 100 μM MgCl$_2$, 100 μM MnCl$_2$, 100 μM CaCl$_2$, 1 mg/ml of BSA in 50 mM HEPES, pH 7.5) were initially introduced, and the substances to be tested were added in 10 μl of binding buffer and incubated for 20 minutes. The controls used were antibodies against VCAM-1 (BBT, No. BBA6) and against VLA4 (Immunotech, No. 0764).

2.6 U937 cells were incubated in Fc receptor blocking buffer for 20 minutes and then added by pipette in a concentration of 1×10$^6$/ml and in an amount of 100 μl per well (final volume 125 μl/well).

2.7 The plates were slowly immersed at an angle of 450 in stop buffer (100 mM NaCl, 100 μM MgCl$_2$, 100 μM MnCl$_2$, 100 μM CaCl$_2$ in 25 mM tris, pH 7.5) and shaken off. The process was repeated.

2.8 50 μl/well of a dye solution (16.7 μg/ml of Hoechst Dye 33258, 4% formaldehyde, 0.5% Triton-X-100 in PBS) were then incubated on the plates for 15 minutes.

2.9 The plates were shaken off and slowly immersed at an angle of 45° in stop buffer (100 mM NaCl, 100 μM MgCl$_2$, 100 μM MnCl$_2$, 100 μM CaCl$_2$ in 25 mM tris, pH 7.5). The process was repeated. Then, with the liquid, measurements were made in a cytofluorimeter (Millipore) (sensitivity: 5, filter: excitation wavelength: 360 nm, emission wavelength: 460 nm).

The intensity of the light emitted by the stained U937 cells is a measure of the number of the U937 cells adherent to the hVCAM-1 (1–3)-IgG and remaining on the plate and thus a measure of the ability of the added test substance to inhibit this adhesion. From the inhibition of the adhesion at various concentrations of the test substance, the concentration IC$_{50}$ was calculated which leads to a 50% inhibition of adhesion.

The following test results were obtained:

| Example | U937/VCAM-1 cell adhesion test IC$_{50}$ (μM) |
| --- | --- |
| 1 | 1.25 |
| 3 | 11.5 |
| 4 | 10.5 |
| 5 | 0.73 |

The disclosure of German Application 19741873.2, filed Sep. 23, 1997, for which benefit under 35 U.S.C.§119 is claimed, is incorporated by reference in its entirety.

Although only certain exemplary embodiments of this invention have been described in detail above, those skilled in the art will readily appreciate that many modifications are possible in the exemplary embodiments without materially departing from the teachings and advantages of this invention. Accordingly, all such modifications are intended to be included within the scope of this invention.

We claim:

1. A compound of the formula I

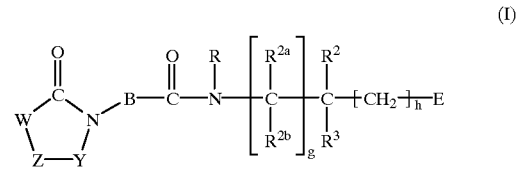

(I)

in which

W is R$^1$—A—C(R$^{13}$) or R$^1$—A—CH═C;

Y is a carbonyl group, thiocarbonyl group, or methylene group;

Z is N(R$^0$), oxygen, sulfur or a methylene group;

A is a divalent radical selected from the group consisting of (C$_1$–C$_6$)-alkylene, (C$_3$–C$_7$)-cycloalkylene, phenylene, phenylene-(C$_1$–C$_6$)-alkyl, (C$_1$–C$_6$)-alkylene-phenyl, phenylene-(C$_2$–C$_6$)-alkenyl, and a divalent radical of a 5-membered or 6-membered saturated or unsaturated heterocycle which contains one or two nitrogen atoms and is unsubstituted or monosubstituted or disubstituted by (C$_1$–C$_6$)-alkyl or doubly bonded oxygen or sulfur;

B is a divalent (C$_1$–C$_6$)-alkylene radical which is unsubstituted or substituted by (C$_1$–C$_8$)-alkyl, (C$_2$–C$_8$)-alkenyl, (C$_2$–C$_8$)-alkynyl, (C$_3$–C$_{10}$)-cycloalkyl, (C$_3$–C$_{10}$)-cycloalkyl-(C$_1$–C$_6$)-alkyl, unsubstituted or substituted (C$_6$–C$_{14}$)-aryl, (C$_6$–C$_{14}$)-aryl-(C$_1$–C$_6$)-alkyl unsubstituted or substituted in the aryl radical, unsubstituted or substituted heteroaryl, or heteroaryl-(C$_1$–C$_6$)-alkyl unsubstituted or substituted in the heteroaryl radical;

E and E$^a$ independently of one another are tetrazolyl, (R$^d$O)$_2$P(O), HOS(O)$_2$, R$^9$NHS(O)$_2$,or R$^{10}$OCO;

R$^0$ is hydrogen, (C$_1$–C$_8$)-alkyl, (C$_3$–C$_{12}$)-cycloalkyl, (C$_3$–C$_{12}$)-cycloalkyl-(C$_1$–C$_8$)-allyl, (C$_6$–C$_{12}$)-bicycloalkyl, (C$_6$–C$_{12}$)-bicycloalkyl-(C$_1$–C$_8$)-alkyl, (C$_6$–C$_{12}$)-tricycloalkyl, (C$_6$–C$_{12}$)-tricycloalkyl-(C$_1$–C$_8$)-alkyl, unsubstituted or substituted (C$_6$–C$_{14}$)-aryl, (C$_6$–C$_{14}$)-aryl-(C$_1$–C$_8$)-alkyl unsubstituted or substituted in the aryl radical, unsubstituted or substituted heteroaryl, heteroaryl-(C$_1$–C$_8$)-alkyl unsubstituted or substituted in the heteroaryl radical, H—CO, (C$_1$–C$_8$)- alkyl-CO, $(C_3–C_{12})$-cycloalkyl-CO, $(C_3–C_{12})$-cycloalkyl-$(C_1–C_8)$-alkyl-CO, $(C_6–C_{12})$-bicycloalkyl-CO, $(C_6–C_{12})$-bicycloalkyl-$(C_1–C_8)$-alkyl-CO, $(C_6–C_{12})$-tricycloalkyl-CO, $(C_6–C_{12})$-tricycloalkyl-$(C_1–C_8)$-alkyl-CO, unsubstituted or substituted $(C_6–C_{14})$-aryl-CO, $(C_6–C_{14})$-aryl-$(C_1–C_8)$-alkyl-CO unsubstituted or substituted in the aryl radical, unsubstituted or substituted heteroaryl-CO, heteroaryl-$(C_1–C_8)$-alkyl-CO unsubstituted or substituted in the heteroaryl radical, $(C_1–C_8)$-alkyl-S(O)$_n$, $(C_3–C_{12})$-cycloalkyl-S(O)$_n$, $(C_3–C_{12})$-cycloalkyl-$(C_1–C_8)$-alkyl-S(O)$_n$, $(C_6–C_{12})$-bicycloalkyl-S(O)$_n$, $(C_6–C_{12})$-bicycloayl-$(C_1–C_8)$-alkyl-S(O)$_n$, $(C_6–C_{12})$-tricycloalkyl-S(O)$_n$, $(C_6–C_{12})$-tricycloalkyl-$(C_1–C_8)$-alkyl-S(O)$_n$, unsubstituted or substituted $(C_6–C_{14})$-aryl-S(O)$_n$, $(C_6–C_{14})$-aryl-$(C_1–C_8)$-alkyl-S(O)$_n$ unsubstituted or substituted in the aryl radical, unsubstituted or substituted heteroaryl-S(O)$_n$ or heteroaryl-$(C_{1–C8})$-alkyl-S(O)$_n$ unsubstituted or substituted in the heteroaryl radical, where n is 1 or 2;

R, $R^a$, $R^b$, $R^c$ and $R^d$ independently of one another are hydrogen, $(C_1–C_8)$-alkyl, $(C_3–C_8)$-cycloalkyl, $(C_3–C_8)$-cycloalkyl-$(C_1–C_8)$-alkyl, unsubstituted or substituted $(C_6–C_{14})$-aryl, or $(C_6–C_{14})$-aryl-$(C_1–C_8)$-alkyl unsubstituted or substituted in the aryl radical;

$R^1$ is X—NH—C(=NH)—$(CH_2)_p$ or $X^1$—NH—$(CH_2)_p$, where p is 0, 1, 2, or 3;

X is hydrogen, $(C_1–C_6)$-alkyl, $(C_1–C_6)$-alkylcarbonyl, $(C_1–C_6)$-alkoxycarbonyl, $(C_1–C_{18})$-alkylcarbonyloxy-$(C_1–C_6)$-alkoxycarbonyl, unsubstituted or substituted $(C_6–C_{14})$-arylcarbonyl, unsubstituted or substituted $(C_6–C_{14})$-aryloxycarbonyl, $(C_6–C_{14})$-aryl-$(C_1–C_6)$-alkoxycarbonyl which unsubstituted or substituted in the aryl radical, $(R^dO)_2P(O)$, cyano, hydroxyl, $(C_1–C_6)$-alkoxy, $(C_6–C_{14})$-aryl-$(C_1–C_6)$-alkoxy which unsubstituted or substituted in the aryl radical, or amino;

$X^1$ has one of the meanings of X or is R'—NH—C(=N—R"), where R' and R" independently of one another have the meanings of X;

$R^2$, $R^{2a}$ and $R^{2b}$ independently of one another are hydrogen, $(C_1–C_8)$-alkyl, unsubstituted or substituted $(C_6–C_{14})$-aryl, $(C_6–C_{14})$-aryl-$(C_1–C_8)$-alkyl unsubstituted or substituted in the aryl radical, $(C_3–C_8)$-cycloalkyl, or $(C_3–C_8)$-cycloalkyl-$(C_1–C_8)$-alkyl;

$R^3$ is $R^{11}$NH, $(C_9–C_{12})$-cycloalkyl, $(C_1–C_8)$-cycloalkyl-$(C_1–C_8)$-alkyl, $(C_6–C_{12})$-bicycloalkyl, $(C_6–C_{12})$-bicycloalkyl-$(C_1–C_8)$-alkyl, $(C_6–C_{12})$-tricycloalkyl, $(C_6–C_{12})$-tricycloalkyl-$(C_1–C_8)$-alkyl, CO—N($R^a$)—$R^4$—$E^a$, or CO—$R^5$—$R^6$—$R^7$;

where, however, $R^3$ cannot be 1-adamantyl if simultaneously W is $R^1$—A—C($R^{13}$), $R^1$—A is 4-amidinophenyl, $R^{13}$ is methyl, Z is NH, Y is a carbonyl group, B is $CH_2$, R and $R^2$ are hydrogen, E is hydroxycarbonyl, g is 0 and h is 1 and, both with respect to the asymmetric carbon atom in the dioxoimidazolidine ring and with respect to the carbon atom that carries the radicals $R^2$ and $R^3$, the R form and the S form are present in the molar ratio 1:1;

$R^4$ is a divalent $(C_1–C_4)$-alkylene radical which is substituted by a radical selected from the group consisting of $R^{11}$NH, $(C_9–C_{12})$-cycloalkyl, $(C_9–C_{12})$-cycloalkyl-$(C_1–C_8)$, $(C_6–C_{12})$-bicycloalkyl, $(C_6–C_{12})$-bicycloalkyl-$(C_1–C_8)$-alkyl, $(C_6–C_{12})$-tricycloalkyl, and $(C_6–C_{12})$-tricycloalkyl-$(C_1–C_8)$-alkyl and which additionally substituted by one or two identical or different $(C_1–C_4)$-alkyl radicals;

$R^5$ is the divalent radical of a natural or unnatural amino acid, an imino acid or an azaamino acid, where free functional groups are unprotected or protected by protective groups or acid groups are present as esters or amides, and where in the case of an amino acid or azaamino acid the nitrogen atom of the N-terminal amino group carries a radical $R^b$;

$R^6$ independently of $R^5$ has one of the meanings of $R^5$ or is a direct bond;

$R^7$ is $R^8$—NH or Het;

$R^8$ is $(C_3–C_{12})$-cycloalkyl, $(C_3–C_{12})$-cycloalkyl-$(C_6–C_{12})$-alkyl, $(C_6–C_{12})$-bicycloalkyl, $(C_6–C_{12})$-bicycloalkyl-$(C_1–C_8)$-alkyl, $(C_6–C_{12})$-tricycloalkyl, or $(C_6–C_{12})$-tricycloalkyl-$(C_1–C_8)$-alkyl;

$R^9$ is hydrogen, aminocarbonyl, $(C_1–C_{18})$-alkylaminocarbonyl, $(C_3–C_8)$-cycloalkylaminocarbonyl, unsubstituted or substituted $(C_6–C_{14})$-arylaminocarbonyl, $(C_1–C_{18})$-alkyl, unsubstituted or substituted $(C_6–C_{14})$-aryl, $(C_6–C_{14})$-aryl-$(C_1–C_8)$-alkyl unsubstituted or substituted in the aryl radical, $(C_3–C_{12})$-cycloalkyl, $(C_3–C_{12})$-cycloalkyl-$(C_1–C_8)$-alkyl, $(C_6–C_{12})$-bicycloalkyl, $(C_6–C_{12})$-bicycloalkyl-$(C_1–C_8)$-alkyl, $(C_6–C_{12})$-tricycloalkyl, or $(C_6–C_{12})$-tricycloalkyl-$(C_1–C_8)$-alkyl;

$R^{10}$ is hydroxyl, $(C_1–C_8)$-alkoxy, $(C_6–C_{14})$-aryl-$(C_1–C_8)$-alkoxy which is unsubstituted or substituted in the aryl radical, unsubstituted or substituted $(C_6–C_{14})$-aryloxy, $(C_1–C_8)$-alkylcarbonyloxy-$(C_1–C_6)$-alkoxy, $(C_6–C_{14})$-arylcarbonyloxy-$(C_1–C_6)$-alkoxy, amino, mono- or di-(($C_1–C_8)$-alkyl)-amino, $R^8$—NH or Het;

$R^{11}$ is $R^{12}$NH—CO, $R^{12}$—NH—CS, $R^{14a}$)—CO, $R^{14b}$CO, $R^{14c}$S(O), $R^{14d}$S(O)$_2$, $R^{14e}$NH—S(O) or $R^{14f}$NH—S(O)$_2$;

$R^{12}$ is unsubstituted or substituted $(C_6–C_{14})$-aryl, $(C_6–C_{14})$-aryl-$(C_1–C_8)$-alkyl which is unsubstituted or substituted in the aryl radical, unsubstituted or substituted heteroaryl, heteroaryl-$(C_1–C_8)$-alkyl unsubstituted or substituted in the heteroaryl radical, $(C_2–C_8)$-alkenyl, $(C_2–C_8)$-alkynyl, or the radical $R^{15}$;

$R^{13}$ is hydrogen, $(C_1–C_6)$-alkyl, unsubstituted or substituted $(C_6–C_{14})$-aryl, $(C_6–C_{14})$-aryl-$(C_1–C_8)$-alkyl unsubstituted or substituted in the aryl radical, $(C_3–C_8)$-cycloalkyl or $(C_3–C_8)$-cycloalkyl-$(C_1–C_8)$-alkyl;

$R^{14a}$ is unsubstituted or substituted heteroaryl, heteroaryl-$(C_1–C_8)$-alkyl unsubstituted or substituted in the heteroaryl radical, or $R^{15}$;

$R^{14b}$ and $R^{14d}$ independently of one another are $(C_6–C_{14})$-aryl-$(C_1–C_8)$-alkyl unsubstituted or substituted in the aryl radical, unsubstituted or substituted heteroaryl, heteroaryl-$(C_1–C_8)$-alkyl unsubstituted or substituted in the heteroaryl radical, or $R^{15}$;

$R^{14c}$ and $R^{14e}$ independently of one another are $(C_1–C_8)$-alkyl, unsubstituted or substituted $(C_6–C_{14})$-aryl, $(C_6–C_{14})$-aryl-$(C_1–C_8)$-alkyl which is unsubstituted or substituted in the aryl radical, unsubstituted or substituted heteroaryl, heteroaryl-$(C_1–C_8)$-alkyl unsubstituted or substituted in the heteroaryl radical, or the radical $R^{15}$;

$R^{14f}$ is $(C_6–C_{14})$-aryl-$(C_1–C_8)$-alkyl unsubstituted or substituted in the aryl radical, unsubstituted or substituted heteroaryl, heteroaryl-$(C_1–C_8)$-alkyl unsubstituted or substituted in the heteroaryl radical, $(C_9–C_{12})$-cycloalkyl-$(C_1–C_8)$-alkyl, $(C_6–C_{12})$-bicycloalkyl, $(C_6–C_{12})$-bicycloalkyl-$(C_1–C_8)$-alkyl, $(C_6–C_{12})$-tricycloalkyl, or $(C_6–C_{12})$-tricycloalkyl-$(C_1–C_8)$-alkyl;

$R^{15}$ is $R^{16}$-($C_1$–$C_6$)-alkyl or $R^{16}$;

$R^{16}$ is the radical of a 3-membered to 12-membered monocyclic ring or the radical of a 6-membered to 24-membered bicyclic or tricyclic ring, where the ring is saturated or partially unsaturated and contains zero, one, two, three or four identical or different ring heteroatoms selected from the group consisting of nitrogen, oxygen, and sulfur and is unsubstituted or substituted by one or more identical or different substituents selected from the group consisting of ($C_1$–$C_4$)-alkyl and oxo;

Het is the radical of a 5-membered to 10-membered monocyclic or polycyclic heterocycle bonded via a ring nitrogen atom, which aromatic or partially unsaturated or saturated and contains zero, one, two, three or four identical or different additional ring heteroatoms selected from the group consisting of oxygen, nitrogen, and sulfur and which is unsubstituted or substituted on carbon atoms and additional ring nitrogen atoms, it being possible for substituents on additional ring nitrogen atoms to be identical or different radicals $R^c$, $R^c$CO or $R^c$O—CO;

g and h independently of one another are 0 or 1;

in any of its stereoisomeric forms mixtures thereof in any ratios, or a physiologically tolerable salt of the compound.

2. A compound of the formula I as claimed in claim 1, in which W is $R^1$—A—C($R^{13}$) and therein A is a divalent radical selected from the group of cyclohexylene, phenylene, and phenylenemethyl;

Y is a carbonyl group;

Z is N($R^0$);

B is a divalent methylene radical or ethylene radical, both radicals being unsubstituted or being substituted by a radical selected from the group consisting of ($C_1$–$C_8$)-alkyl, ($C_3$–$C_8$)-cycloalkyl, ($C_3$–$C_8$)-cycloalkyl-($C_1$–$C_4$)-alkyl, unsubstituted or substituted ($C_6$–$C_{10}$)-aryl, ($C_6$–$C_{10}$)-aryl-($C_1$–$C_4$)-alkyl unsubstituted or substituted in the aryl radical, unsubstituted or substituted heteroaryl, and heteroaryl-($C_1$–$C_4$)-alkyl unsubstituted or substituted in the heteroaryl radical;

E and $E^a$ independently of one another are $R^{10}$CO;

R, $R^a$, and $R^b$ independently of one another are hydrogen, ($C_1$–$C_6$)-alkyl, or benzyl;

$R^c$ is hydrogen, ($C_1$–$C_6$)-alkyl, ($C_5$–$C_6$)-cycloalkyl, ($C_5$–$C_6$)-cycloalkyl-($C_1$–$C_2$)-alkyl, unsubstituted or substituted phenyl, or phenyl-($C_1$–$C_2$)-alkyl unsubstituted or substituted in the phenyl radical;

$R^0$ is ($C_1$–$C_6$)-alkyl, ($C_5$–$C_{10}$)-cycloalkyl, ($C_5$–$C_{10}$)-cycloalkyl-($C_1$–$C_4$)-alkyl, ($C_7$–$C_{12}$)-bicycloalkyl, ($C_7$–$C_{12}$)-bicycloalkyl-($C_1$–$C_4$)-alkyl, ($C_{10}$–$C_{12}$)-tricycloalkyl, ($C_{10}$–$C_{12}$)-tricycloalkyl-($C_1$–$C_4$)-alkyl, unsubstituted or substituted ($C_6$–$C_{12}$)-aryl, ($C_6$–$C_{12}$)-aryl-($C_1$–$C_4$)-alkyl unsubstituted or substituted in the aryl radical, unsubstituted or substituted heteroaryl, heteroaryl-($C_1$–$C_4$)-alkyl unsubstituted or substituted in the heteroaryl radical, ($C_1$–$C_6$)-alkyl-CO, ($C_5$–$C_{10}$)-cycloalkyl-CO, ($C_5$–$C_{10}$)-cycloalkyl-($C_1$–$C_4$)-alkyl-CO, ($C_7$–$C_{12}$)-bicycloalkyl-CO, ($C_7$–$C_{12}$)-bicycloalkyl-($C_1$–$C_4$)-alkyl-CO, ($C_{10}$–$C_{12}$)-tricycloalkyl-CO, ($C_{10}$–$C_{12}$)-tricycloalkyl-($C_1$–$C_4$)-alkyl-CO, unsubstituted or substituted ($C_6$–$C_{12}$)-aryl-CO, ($C_6$–$C_{10}$)-aryl-($C_1$–$C_4$)-alkyl-CO unsubstituted or substituted in the aryl radical, unsubstituted or substituted heteroaryl-CO, heteroaryl-($C_1$–$C_4$)-alkyl-CO unsubstituted or substituted in the heteroaryl radical, ($C_1$–$C_6$)-alkyl-S(O)$_n$, ($C_5$–$C_{10}$)-cycloalkyl-S(O)$_n$, ($C_5$–$C_{10}$)-cycloalkyl-($C_1$–$C_4$)-alkyl-S(O)$_n$, ($C_7$–$C_{12}$)-bicycloalkyl-S(O)$_n$, ($C_7$–$C_{12}$)-bicycloalkyl-($C_1$–$C_4$)-alkyl-S(O)$_n$, ($C_{10}$–$C_{12}$)-tricycloalkyl-S(O)$_n$, ($C_{10}$–$C_{12}$)-tricycloalkyl-($C_1$–$C_4$)-alkyl-S(O)$_n$, unsubstituted or substituted ($C_6$–$C_{12}$)-aryl-S(O)$_n$, ($C_6$–$C_{12}$)-aryl-($C_1$–$C_4$)-alkyl-S(O)$_n$ unsubstituted or substituted in the aryl radical, unsubstituted or substituted heteroaryl-S(O)$_n$ or heteroaryl-($C_1$–$C_4$)-alkyl-S(O)$_n$ unsubstituted or substituted in the heteroaryl radical, where n is 1 or 2;

$R^1$ is X—NH—C(=NH), X—NH—C(=NX)—NH or X—NH—CH$_2$;

X is hydrogen, ($C_1$–$C_6$)-alkylcarbonyl, ($C_1$–$C_6$)-alkoxycarbonyl, ($C_1$–$C_8$)-alkylcarbonyloxy-($C_1$–$C_6$)-alkoxycarbonyl, ($C_6$–$C_{14}$)-aryl-($C_1$–$C_6$)-alkoxycarbonyl or hydroxyl;

$R^2$, $R^{2a}$ and $R^{2b}$ independently of one another are hydrogen or ($C_1$–$C_8$)-alkyl;

$R^3$ is $R^{11}$NH, ($C_{10}$–$C_{12}$)-cycloalkyl, ($C_{10}$–$C_{12}$)-cycloalkyl-($C_1$–$C_4$)-alkyl, ($C_7$–$C_{12}$)-bicycloalkyl, ($C_7$–$C_{12}$)-bicycloalkyl-($C_1$–$C_4$)-alkyl, ($C_{10}$–$C_{12}$)-tricycloalkyl, ($C_{10}$–$C_{12}$)-tricycloalkyl-($C_1$–$C_4$)-alkyl, CO—N($R^a$)—$R^4$—$E^a$ or CO—$R^5$—$R^6$—Het;

$R^{10}$ is hydroxyl, ($C_1$–$C_6$)-alkoxy, ($C_6$–$C_{10}$)-aryl-($C_1$–$C_8$)-alkoxy which is unsubstituted or substituted in the aryl radical, unsubstituted or substituted ($C_6$–$C_{10}$)-aryloxy or ($C_1$–$C_8$)-alkylcarbonyloxy-($C_1$–$C_6$)-alkoxy;

$R^{11}$ is $R^{12}$NH—CO, $R^{14a}$O—CO, $R^{14b}$CO, $R^{14c}$S(O) or $R^{14d}$S(O)$_2$;

$R^{14a}$ is heteroaryl-($C_1$–$C_2$)-alkyl unsubstituted or substituted in the heteroaryl radical, or the radical $R^{15}$;

$R^{14b}$ and $R^{14d}$ independently of one another are ($C_6$–$C_{10}$)-aryl-($C_1$–$C_2$)-alkyl unsubstituted or substituted in the aryl radical, heteroaryl-($C_1$–$C_2$)-alkyl unsubstituted or substituted in the heteroaryl radical, or the radical $R^{15}$;

$R^{14c}$ is ($C_1$–$C_6$)-alkyl, ($C_6$–$C_{10}$)-aryl-($C_1$–$C_2$)-alkyl which is unsubstituted or substituted in the aryl radical, or the radical $R^{15}$;

$R^{15}$ is $R^{16}$—($C_1$–$C_4$)-alkyl or is $R^{16}$;

$R^{16}$ is the radical of a 5-membered to 10-membered monocyclic ring or the radical of a 6-membered to 14-membered bicyclic or tricyclic ring, where the rings is saturated and contains zero, one or two identical or different ring heteroatoms selected from the group of nitrogen, oxygen, and sulfur and is unsubstituted or substituted by one, two, three or four identical or different ($C_1$–$C_4$)-alkyl radicals;

Het is the radical of a 5-membered or 10-membered monocyclic heterocycle bonded via a ring nitrogen atom, which is aromatic or partially unsaturated or saturated and contains zero, one or two identical or different additional ring heteroatoms selected from the group consisting of oxygen, nitrogen and sulfur and which is unsubstituted or substituted where substituents on ring nitrogen atoms are identical or different radicals $R^c$, $R^c$CO $R^c$O—CO one or more identical or different substituents selected from the group consisting of ($C_1$–$C_6$)-alkyl, ($C_1$–$C_6$)-alkoxy, trifluoromethyl, phenyl, and benzyl;

in any stereoisomeric forms mixtures thereof in any ratios, or a physiologically tolerable salt of the compound.

3. A compound of the formula I as claimed in claim 1, in which W is $R^1$—A—C($R^{13}$) and $R^{13}$ is ($C_1$–$C_6$)-alkyl, $(C_6-C_{14})$-aryl-$(C_1-C_8)$-alkyl unsubstituted or substituted in the aryl radical, or $(C_3-C_8)$-cycloalkyl; in any of its stereoisomeric forms mixtures thereof in any ratios, or a physiologically tolerable salt of the compound.

4. A compound of the formula I as claimed in claim 1, in which $R^3$ is $R^{11}NH$, $(C_{10}-C_{12})$-cycloalkyl, $(C_{10}-C_{12})$-cycloalkyl-$(C_1-C_4)$-alkyl, $(C_7-C_{12})$-bicycloalkyl, $(C_7-C_{12})$-bicycloalkyl-$(C_1-C_4)$-alkyl, $(C_{10}-C_{12})$-tricycloalkyl, $(C_{10}-C_{12})$-tricycloalkyl-$(C_1-C_4)$-alkyl, CO—N($R^a$)—$R^4E^a$ or CO—$R^5$—$R^6$—Het;

$R^{11}$ is $R^{15}O$—CO or $R^{15}S(O)_2$;

$R^{15}$ is $R^{16}$-$(C_1-C_3)$-alkyl or $R^{16}$;

$R^{16}$ is the radical of a 5-membered to 6-membered monocyclic ring or the radical of a 6-membered to 12-membered bicyclic or tricyclic ring, where the ring is saturated and contains zero, one or two identical or different ring heteroatoms selected from the group consisting of nitrogen and oxygen and is unsubstituted or substituted by one, two or three identical or different $(C_1-C_4)$-alkyl radicals;

in any of its stereoisomeric forms or mixtures thereof in any ratios, or a physiologically tolerable salt thereof.

5. A compound of the formula I as claimed in claim 1, in which

W is $R^1$—A—C($R^{13}$);

Y is a carbonyl group;

Z is N($R^0$);

A is a divalent radical selected from the group consisting of cyclohexylene, phenylene and phenylenemethyl;

B is a divalent methylene radical which is unsubstituted or substituted by a radical selected from the group consisting of $(C_1-C_8)$-alkyl, $(C_5-C_6)$-cycloalkyl, $(C_5-C_6)$-cycloalkyl-$(C_1-C_4)$-alkyl, unsubstituted or substituted phenyl, phenyl-$(C_1-C_4)$-alkyl unsubstituted or substituted in the phenyl radical, unsubstituted or substituted 5-membered or 6-membered heteroaryl, and heteroaryl-$(C_1-C_4)$-alkyl unsubstituted or substituted in the heteroaryl radical;

E and $E^a$ independently of one another are $R^{10}CO$;

R, $R^a$ and $R^b$ independently of one another are hydrogen or $(C_1-C_4)$-alkyl;

$R^0$ is $(C_1-C_6)$-alkyl, $(C_5-C_6)$-cycloalkyl, $(C_5-C_6)$-cycloalkyl-$(C_1-C_2)$-alkyl, unsubstituted or substituted $(C_6-C_{12})$-aryl, $(C_6-C_{12})$-aryl-$(C_1-C_2)$-alkyl unsubstituted or substituted in the aryl radical, unsubstituted or substituted heteroaryl, heteroaryl-$(C_1-C_2)$-alkyl unsubstituted or substituted in the heteroaryl radical, $(C_1-C_6)$-alkyl-CO, $(C_5-C_6)$-cycloalkyl-CO, $(C_5-C_6)$-cycloalkyl-$(C_1-C_2)$-alkyl-CO, unsubstituted or substituted $(C_6-C_{12})$-aryl-CO, $(C_6-C_{12})$-aryl-$(C_1-C_2)$-alkyl-CO unsubstituted or substituted in the aryl radical, $(C_1-C_6)$-alkyl-S(O)$_n$, $(C_5-C_6)$-cycloalkyl-S(O)$_n$, $(C_5-C_6)$-cycloalkyl-$(C_1-C_2)$-alkyl-S(O)$_n$, unsubstituted or substituted $(C_6-C_{12})$-aryl-S(O)$_n$ or $(C_6-C_{12})$-aryl-$(C_1-C_2)$-alyl-S(O)$_n$ unsubstituted or substituted in the aryl radical, where n is 1 or 2;

$R^1$ is $H_2N$—C(=NH), $H_2N$—C(=N—OH), $CH_3O$—CO—NH—C(=NH), $H_2N$—C(=NH)—NH or $H_2N$—$CH_2$;

$R^2$, $R^{2a}$, and $R^{2b}$ are hydrogen;

$R^3$ is $R^{11}NH$, $(C_{10}-C_{12})$-cycloalkyl, $(C_{10}-C_{12})$-cycloalkyl-$(C_1-C_3)$-alkyl, $(C_7-C_{12})$-bicycloalkyl, $(C_7-C_{12})$-bicycloalkyl-$(C_1-C_3)$-alkyl, $(C_{10}-C_{12})$-tricycloalkyl, $(C_{10}-C_{12})$-tricycloalkyl-$(C_1-C_3)$-alkyl, CO—N($R^a$)—$R^4$—$E^a$ or CO—$R^5$—$R^6$—Het;

$R^{10}$ is hydroxyl, $(C_1-C_4)$-alkoxy, phenoxy, benzyloxy or $(C_1-C_4)$-alkylcarbonyloxy-$(C_1-C_4)$-alkoxy;

$R^{11}$ is $R^{15}O$—CO or $R^{15}S(O)_2$;

$R^{13}$ is $(C_1-C_6)$-alkyl, $(C_3-C_7)$-cycloalkyl, or benzyl;

$R^{15}$ is $R^{16}$—$(C_1-C_3)$-alkyl or $R^{16}$;

$R^{16}$ is the radical of a 5-membered to 6-membered monocyclic ring or the radical of a 6-membered to 12-membered bicyclic or tricyclic ring, where the ring is saturated and contains zero, one or two identical or different ring heteroatoms selected from the group consisting of nitrogen and oxygen is unsubstituted or substituted by one, two or three identical or different $(C_1-C_4)$-alkyl radicals;

Het is the radical of a 5-membered to 6-membered monocyclic heterocycle bonded via a ring nitrogen atom, which is saturated and which contains zero or one additional ring heteroatom selected from the group consisting of oxygen and sulfur and which is unsubstituted or monosubstituted or disubstituted by identical or different substituents selected from the group consisting of $(C_1-C_4)$-alkyl, $(C_1-C_4)$-alkoxy, trifluoromethyl, phenyl, and benzyl;

in any of its stereoisomeric forms mixtures thereof in any ratios, or a physiologically tolerable salt of the compound.

6. A compound of the formula I as claimed in claim 1, in which

W is $R^1$—A—C($R^{13}$) and therein A is the divalent phenylene radical;

Y is a carbonyl group;

Z is N($R^0$);

B is a divalent methylene radical which is unsubstituted or substituted by a radical selected from the group consisting of $(C_1-C_6)$-alkyl, $(C_5-C_6)$-cycloalkyl, $(C_5-C_6)$-cycloalkyl-$(C_1-C_4)$-alkyl, phenyl, benzyl, and phenylethyl;

E is $R^{10}CO$;

R, $R^a$, and $R^b$ independently of one another are hydrogen or $(C_1-C_4)$-alkyl;

$R^0$ is $(C_1-C_6)$-alkyl, $(C_6-C_{12})$-aryl-$(C_1-C_2)$-alkyl unsubstituted or substituted in the aryl radical, $(C_1-C_6)$-alkyl-S(O)$_2$, or $(C_6-C_{12})$-aryl-S(O)$_2$ unsubstituted or substituted in the aryl radical;

$R^1$ is $H_2N$—C(=NH), $H_2N$—C(=N—OH), $CH_3O$—CO—NH—C(=NH), $H_2N$—C(=NH)—NH or $H_2N$—$CH_2$;

$R^2$, $R^{2a}$ and $R^{2b}$ are hydrogen;

$R^3$ is $R^{11}NH$ or CO—$R^5$—Het;

$R^5$ is the divalent radical of a natural or unnatural α-amino acid having a lipophilic side chain, where free functional groups are unprotected or protected by protective groups or acid groups are present as esters or amides, and where the nitrogen atom of the N-terminal amino group carries a radical $R^b$;

$R^{10}$ is hydroxyl, $(C_1-C_4)$-alkoxy, phenoxy, benzyloxy or $(C_1-C_4)$-alkylcarbonyloxy-$(C_1-C_4)$-alkoxy;

$R^{11}$ is $R^{15}O$—CO or $R^{15}S(O)_2$;

$R^{13}$ is $(C_1-C_6)$-alkyl;

$R^{15}$ is $R^{16}$—$(C_1-C_3)$-alkyl or $R^{16}$;

$R^{16}$ is the radical of a 5-membered to 6-membered monocyclic ring or the radical of a 7-membered to 12-membered bicyclic or tricyclic ring, where the ring is saturated and contains zero, one or two identical or different ring heteroatoms selected from the group consisting of oxygen and nitrogen and is unsubstituted or substituted by one or two identical or different ($C_1$–$C_4$)-alkyl radicals;

Het is the radical of a 5-membered or 6-membered monocyclic heterocycle bonded via a ring nitrogen atom, which is saturated and which contains zero or one additional ring heteroatom selected from the group consisting of oxygen and sulfur and which is unsubstituted or substituted by one or two identical or different ($C_1$–$C_4$)-alkyl radicals;

in any of its stereoisomeric forms or mixtures thereof in any ratios, or a physiologically tolerable salt of the compound.

7. A compound of the formula I as claimed in claim 1, in which

W is $R^1$—A—C($R^{13}$) and therein A is the divalent phenylene radical;

Y is a carbonyl group;

Z is N($R^0$);

B is a divalent methylene radical which is unsubstituted or substituted by a radical selected from the group consisting of ($C_1$–$C_6$)-alkyl, ($C_5$–$C_6$)-cycloalkyl-($C_1$–$C_4$)-alkyl, phenyl, benzyl, and phenylethyl;

E is $R^{10}$CO;

R, $R^a$, and $R^b$ independently of one another are hydrogen or methyl;

$R^1$ is ($C_1$–$C_6$)-alkyl or ($C_6$–$C_{12}$)-aryl-($C_1$–$C_2$)-alkyl unsubstituted or substituted in the aryl radical;

$R^1$ is $H_2N$—C(=NH), $H_2N$—C(=NOH), $CH_3$—CO—NH—C(=NH), $H_2NH$—C(=NH)—NH or $H_2NH$—$CH_2$;

$R^2$, $R^{2a}$ and $R^{2b}$ are hydrogen;

$R^3$ is $R^{11}$NH or CO—$R^5$—Het;

$R^5$ is the divalent radical of a natural or unnatural α-amino acid having a lipophilic side chain, where free functional groups are unprotected or protected by protective groups or acid groups are present as esters or amides, and where the nitrogen atom of the N-terminal amino group carries a radical $R^b$;

$R^{10}$ is hydroxyl, ($C_1$–$C_4$)-alkoxy, phenoxy, benzyloxy or ($C_1$–$C_4$)-alkylcarbonyloxy-($C_1$–$C_4$)-alkoxy;

$R^{11}$ is $R^{15}$O—CO;

$R^{13}$ is ($C_1$–$C_6$)-alkyl;

$R^{15}$ is $R^{16}$ or $R^{16}$—$CH_2$;

$R^{16}$ is cyclopentyl, cyclohexyl, 1-adamantyl, 2-adamantyl or noradamantyl;

Het is the radical of a 5-membered or 6-membered monocyclic heterocycle bonded via a ring nitrogen atom, which is saturated and which contains zero or one oxygen atom as an additional ring heteroatom and which is unsubstituted or substituted by one or two identical or different ($C_1$–$C_4$)-akyl radicals;

in any of its stereoisomeric forms or mixtures thereof in any ratios, or a physiologically tolerable salt thereof.

8. A process for the preparation of a compound of formula I as claimed in claim 1, which comprises reacting a compound of the formula II

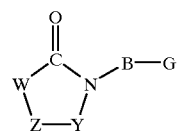

with a compound of the formula III

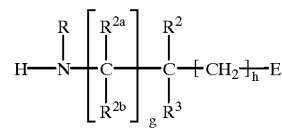

where, in the formulae II and III, the groups W, Y, Z, B, E, R, $R^2$, $R^{2b}$ and $R^3$ as well as g and h are defined as in claim 1, wherein the functional groups are present in protected form or in the form of precursors, and where G is hydroxycarbonyl, ($C_1$–$C_6$)-alkoxycarbonyl or an ester chloride or an active ester.

9. A pharmaceutical comprising a compound of the formula I as claimed in claim 1 or a physiologically tolerable salt thereof.

10. A pharmaceutical preparation which comprises one or more compounds of the formula I as claimed in claim 1 or a physiologically tolerable salt thereof and a pharmaceutically innocuous excipient or additive.

11. A method for the therapy or prophylaxis of inflamation in a mammal in need thereof comprising administering to the mammal a compound of the formula I as claimed in claim 1 or a physiologically tolerable salt thereof.

12. A method for the therapy or prophylaxis of rheumatoid arthritis, of inflammatory bowel disease, of systemic lupus erythematosus, or of inflammatory disorders of the central nervous system, in a mammal, in need thereof, comprising administering to the mammal a compound as claimed in claim 1 or a physiologically tolerable salt thereof.

13. A method for the therapy or prophylaxis of asthma or allergies in a mammal in need thereof, comprising administering to the mammal a compound as claimed in claim 1 or a physiologically tolerable salt thereof.

14. A method for the therapy or prophylaxis of a cardiovascular disorder, arteriosclerosis, of restenoses or of diabetes, for the prevention of damage to an organ transplant, for the inhibition of tumor growth or formation of tumor metastases, or for the therapy of malaria in a mammal in need thereof, comprising administering to the mammal a compound as claimed in claim 1 or a physiologically tolerable salt thereof.

15. A method for the inhibition of the adhesion or migration of leucocytes or the inhibition of the VLA-4 receptor in a mammal in need thereof, comprising administering to the mammal a compound as claimed in claim 1 or a physiologically tolerable salt thereof.

* * * * *